United States Patent
Kurihara et al.

(10) Patent No.: US 10,179,924 B2
(45) Date of Patent: Jan. 15, 2019

(54) METHOD FOR PRODUCING SUGAR SOLUTION

(75) Inventors: Hiroyuki Kurihara, Kamakura (JP); Junpei Kishimoto, Kamakura (JP); Katsushige Yamada, Kamakura (JP)

(73) Assignee: Toray Industries, Inc. (JP)

(*) Notice: Subject to any disclaimer, the term of this patent is extended or adjusted under 35 U.S.C. 154(b) by 85 days.

(21) Appl. No.: 14/007,438

(22) PCT Filed: Mar. 28, 2012

(86) PCT No.: PCT/JP2012/058076
§ 371 (c)(1),
(2), (4) Date: Sep. 25, 2013

(87) PCT Pub. No.: WO2012/133495
PCT Pub. Date: Oct. 4, 2012

(65) Prior Publication Data
US 2014/0017736 A1   Jan. 16, 2014

(30) Foreign Application Priority Data

Mar. 29, 2011  (JP) .................. 2011-072021

(51) Int. Cl.
*C12P 19/14* (2006.01)
*C12P 19/02* (2006.01)

(52) U.S. Cl.
CPC .............. *C12P 19/14* (2013.01); *C12P 19/02* (2013.01)

(58) Field of Classification Search
None
See application file for complete search history.

(56) References Cited

U.S. PATENT DOCUMENTS

| 2011/0250637 A1 | 10/2011 | Kurihara et al. |
| 2013/0004994 A1 | 1/2013 | Hanakawa et al. |
| 2013/0059345 A1 | 3/2013 | Kurihara et al. |

FOREIGN PATENT DOCUMENTS

| JP | 63-087994 A | 4/1988 |
| JP | 2006-087319 A | 4/2006 |
| JP | 2008-161125 A | 7/2008 |
| JP | 2008-206484 A | 9/2008 |
| JP | 2008-535664 A | 9/2008 |
| JP | 2009-189291 A | 8/2009 |
| WO | 2010/067785 A1 | 6/2010 |
| WO | 2011/111451 A1 | 9/2011 |
| WO | 2011/115039 A1 | 9/2011 |
| WO | 2012/029842 A1 | 3/2012 |

OTHER PUBLICATIONS

Tokuyasu et al., Pretreatment of microcrystalline cellulose flakes with CaCl2 increases the surface area, and thus improves enzymatic saccharification, Carbohydrate Research 343 (2008) 1232-1236.*
Kondo et al., Aqueous counter collision using paired water jets as a novel means of preparing bio-nanofibers, Carbohydrate Polymers, 112 (2014) pp. 284-290.*
Liu et al., Eliminating inhibition of enzymatic hydrolysis by lignosulfonate in unwashed sulfite-pretreated aspen using metal salts, Bioresource Technology, 101 (2010) pp. 9120-9127.*
English translations of a Notification of Reasons for Refusal dated Aug. 2, 2016, and a Decision of Refusal dated Nov. 8, 2016, of corresponding Japanese Patent Application No. 2012-521895.

* cited by examiner

*Primary Examiner* — Jennifer M. H. Tichy
(74) *Attorney, Agent, or Firm* — DLA Piper LLP (US)

(57) ABSTRACT

A method of producing a sugar liquid includes hydrolyzing with a filamentous fungus-derived cellulase a product obtained by adding a water-soluble inorganic salt(s) to a pretreated product of cellulose to a final concentration of 5 to 35 g/L; and subjecting the hydrolysate to solid-liquid separation and filtering the obtained solution component through an ultrafiltration membrane to recover the filamentous fungus-derived cellulase as a non-permeate and to obtain a sugar liquid as a permeate.

20 Claims, 2 Drawing Sheets

METHOD FOR PRODUCING SUGAR SOLUTION

TECHNICAL FIELD

This disclosure relates to a method of producing a sugar liquid from a cellulose-containing biomass.

BACKGROUND

In recent years, methods of producing a sugar liquid by pretreating a cellulose-containing biomass with an acid, hot water, alkali or the like and then adding cellulase thereto to perform hydrolysis have been widely studied. However, these methods of producing a sugar liquid using cellulase have a drawback in that, since a large amount of cellulase is used and cellulase is expensive, the cost of producing the sugar liquid is high.

As methods of solving the problem, methods wherein cellulase used for the hydrolysis of cellulose is recovered and reused have been proposed. Known examples of such methods include a method wherein continuous solid-liquid separation is carried out with a spin filter and the obtained sugar liquid is filtered through an ultrafiltration membrane to recover cellulase (JP 2006-87319 A), a method wherein a surfactant is fed at the stage of enzymatic saccharification, to suppress cellulase adsorption and thereby enhance the recovery efficiency (JP 63-87994 A) and a method wherein the residue produced by enzymatic saccharification is subjected to electric treatment to recover the cellulase component (JP 2008-206484 A), but these methods failed to fundamentally solve the problem.

It could therefore be helpful to reduce the amount of cellulase used for hydrolysis of cellulose during production of a sugar liquid from a cellulose-containing biomass.

SUMMARY

We discovered that addition of a water-soluble inorganic salt(s) to the cellulose hydrolysate to a final concentration of 5 to 35 g/L enables improvement of the amount of recovery of cellulase contained in the cellulose hydrolysate.

We thus provide [1] to [7] below:

[1] A method of producing a sugar liquid, the method comprising the Steps (1) and (2) below:
  Step (1): a step of hydrolyzing with a filamentous fungus-derived cellulase a product obtained by adding a water-soluble inorganic salt(s) to a pretreated product of cellulose to a final concentration within the range of 5 to 35 g/L; and
  Step (2): a step of subjecting the hydrolysate to solid-liquid separation and filtering the obtained solution component through an ultrafiltration membrane, to recover the filamentous fungus-derived cellulase as a non-permeate and to obtain a sugar liquid as a permeate.

[2] The method of producing a sugar liquid according to [1], wherein the water-soluble inorganic salt(s) of Step (1) is/are one or more selected from the group consisting of sodium salts, potassium salts, magnesium salts, calcium salts and ammonium salts.

[3] The method of producing a sugar liquid according to [1] or [2], wherein the water-soluble inorganic salt(s) of Step (1) is/are one or more selected from the group consisting of sodium chloride, potassium chloride, sodium sulfate, magnesium chloride, magnesium sulfate, calcium chloride and ammonium sulfate.

[4] The method of producing a sugar liquid according to any one of [1] to [3], wherein the pretreated product of cellulose of Step (1) is one or more products selected from the group consisting of products obtained by hydrothermal treatment, dilute sulfuric acid treatment or alkali treatment.

[5] The method of producing a sugar liquid according to any one of [1] to [4], wherein the filamentous fungus-derived cellulase is *Trichoderma*-derived cellulase.

[6] The method of producing a sugar liquid according to any one of [1] to [5], further comprising the step of filtering the sugar liquid of Step (2) through a nanofiltration membrane and/or reverse osmosis membrane to remove fermentation inhibitors as a permeate and to obtain a sugar concentrate as a non-permeate.

[7] The method of producing a sugar liquid according to [6], further comprising the step of filtering through a reverse osmosis membrane a permeate obtained by filtering the sugar liquid of Step (2) through a nanofiltration membrane; and reusing the inorganic salt concentrate obtained as a non-permeate as the water-soluble inorganic salt(s) of Step (1).

The enzyme recovery of filamentous fungus-derived cellulase from a cellulose hydrolysate is improved so that the amount of cellulase used in the process for producing a sugar liquid can be reduced.

BRIEF DESCRIPTION OF THE DRAWINGS

FIG. 1 is a schematic process flow diagram wherein a neutralizer is added to ammonia or an acid remaining in a pretreated product of biomass, to thereby prepare a water-soluble inorganic salt(s).

FIG. 2 is a schematic process flow diagram wherein a pretreated product of biomass is subjected to solid-liquid separation, and the separated dilute-sulfuric-acid-treated liquid or ammonia-treated liquid is neutralized, to thereby prepare a water-soluble inorganic salt(s).

DESCRIPTION OF SYMBOLS

Figure 1:
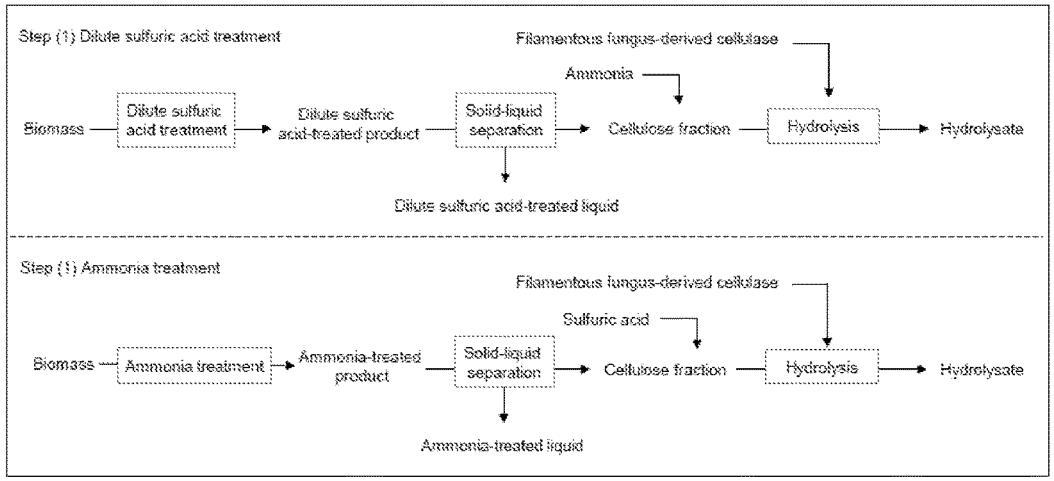
FIG. 1 is a schematic flow diagram showing an example of Step (1) of our method. That is.

1 Incubator
2 Hydrolysis tank
3 Inlet
4 Stirrer
5 Water-soluble-inorganic-salt preparation tank
6 Hydrolysate inlet
7 Press filter
8 Compressor
9 Press filtration filtrate tank
10 Discharge line
11 Microfiltration membrane
12 MF pump
13 Microfiltration membrane filtrate tank
14 UF pump
15 Ultrafiltration membrane
16 Sugar liquid collection line

DETAILED DESCRIPTION

Examples of our methods are described below in detail for each Step.

Step (1)

The pretreated product of cellulose in Step (1) means a cellulose-containing biomass that was pretreated for hydrolysis. Specific examples of the cellulose-containing biomass include herbaceous biomasses such as bagasse, switchgrass, napier grass, *Erianthus*, corn stover, corncob, rice straw, wheat straw and coconut husk; woody biomasses such as trees, poplar, willow and waste building materials; and water environment-derived biomasses such as algae and seaweeds. Such biomasses contain, in addition to cellulose and hemicellulose (hereinafter referred to as "cellulose" as a general term for cellulose and hemicellulose), lignin as aromatic macromolecules. That is, pretreatment of a cellulose-containing biomass is carried out to improve the efficiency of hydrolysis of the biomass by filamentous fungus-derived cellulase, and the product obtained as a result is referred to as a pretreated product of cellulose.

Examples of the pretreatment of a cellulose-containing biomass include acid treatment, sulfuric acid treatment, dilute sulfuric acid treatment, alkali treatment, hydrothermal treatment, subcritical water treatment, pulverization treatment, steaming treatment and drying treatment. The pretreatment is preferably hydrothermal treatment, dilute sulfuric acid treatment or alkali treatment since alkali treatment, hydrothermal treatment and dilute sulfuric acid treatment show better enzymatic saccharification efficiencies and require smaller amounts of enzyme compared to the other methods.

In the case of hydrothermal treatment, water is added such that the concentration of the cellulose-containing biomass is 0.1 to 50% by weight, and the resulting mixture is treated at a temperature of 100 to 400° C. for 1 second to 60 minutes. By treatment under such temperature conditions, hydrolysis of cellulose occurs. The number of times of the treatment is not restricted, and 1 or more times of the treatment may be carried out. In particular, in cases where the treatment is carried out 2 or more times, the conditions for the first treatment may be different from those for the second and later treatments.

In the case of dilute sulfuric acid treatment, the concentration of sulfuric acid is preferably 0.1 to 15% by weight, more preferably 0.5 to 5% by weight. The reaction temperature may be set at 100 to 300° C., and is preferably set at 120 to 250° C. The reaction time may be set to 1 second to 60 minutes. The number of times of the treatment is not restricted, and 1 or more times of the treatment may be carried out. In particular, in cases where the treatment is carried out 2 or more times, the conditions for the first treatment may be different from those for the second and later treatments. Since the hydrolysate obtained by dilute sulfuric acid treatment contains acid, neutralization is necessary to further carry out hydrolysis reaction with cellulase or to use the hydrolysate as a fermentation feedstock.

The alkali treatment is a method wherein an alkali selected from sodium hydroxide, calcium hydroxide and ammonia is allowed to act on a cellulose-containing biomass. As the alkali used in the alkali treatment, ammonia may be especially preferably used. The ammonia treatment may be carried out by methods described in JP 2008-161125 A and JP 2008-535664 A. For example, ammonia is added to a cellulose-containing biomass at a concentration within the range of 0.1 to 15% by weight, and the treatment is carried out at 4 to 200° C., preferably 90 to 150° C. The ammonia to be added may be in the state of either liquid or gas. Further, the form of the ammonia to be added may be either pure ammonia or aqueous ammonia. The number of times of the treatment is not restricted, and 1 or more times of the treatment may be carried out. In cases where the treatment is carried out 2 or more times, the conditions for the first treatment may be different from those for the second and later treatments. The treated product obtained by ammonia treatment needs to be subjected to neutralization of ammonia or removal of ammonia to further carry out enzymatic hydrolysis reaction. The neutralization of ammonia may be carried out either after removal of the solid component from the hydrolysate by solid-liquid separation or in a state where the solid component is contained. The acid reagent to be used for the neutralization is not restricted. For removal of ammonia, the ammonia-treated product may be kept under reduced pressure to allow evaporation of ammonia into the gas state . The removed ammonia may be recovered and reused.

In Step (1), a water-soluble inorganic salt(s) is/are added to the above-described pretreated product of cellulose to a final concentration of 5 to 35 g/L. In cases where the final concentration of the water-soluble inorganic salt(s) is less than 5 g/L, the salt(s) is/are not effective for the recovery of filamentous-fungal cellulase in Step (2) described later, while in cases where the final concentration exceeds 35 g/L, the activity itself of the filamentous-fungal cellulase is low and the amount of sugar produced is small, which is not preferred.

In general, a salt means a compound formed by ionic bonding of an acid-derived anion(s) with a base-derived cation(s). In particular, an "inorganic salt" means a "salt that does not contain a carbon atom," which is a compound formed by ionic bonding of a chloride ion(s) ($Cl^-$), nitrate ion(s) ($NO_3^-$), phosphate ion(s) ($PO_4^{3-}$, $H_2PO_4^-$, $HPO_4^{2-}$), sulfate ion(s) ($SO_4^{2-}$) and/or the like with a sodium ion(s) ($Na^+$), potassium ion(s) ($K^+$), ammonium ion(s) ($NH_4^+$), calcium ion(s) ($Ca^{2+}$), magnesium ion(s) ($Mg^{2+}$) and/or the like. Among the above-described inorganic salts, a "water-soluble inorganic salt" means an inorganic salt having a solubility in water (water solubility) of not less than "50 g/L." In particular, calcium sulfate (gypsum) ($CaSO_4$) and calcium phosphate ($CaHPO_4$, $Ca(H_2PO_4)_2$, $Ca_3(PO_4)_2$) are classified into water-insoluble inorganic salts because of their water solubilities of less than "50 g/L", so that they are excluded from the water-soluble inorganic salts.

Examples of salts other than water-soluble inorganic salts include organic salts (or water-soluble organic salts). An organic salt means a compound formed by ionic bonding of an anion(s) derived from an acid(s) containing a carbon atom(s) such as carboxylic acid ($-COO^-$), with a cation(s). Organic salts are distinguished from the inorganic salts. For example, acetates (sodium acetate and the like) and citrates (sodium citrate and the like), which are generally used as buffers in enzymatic hydrolysis of cellulose, are organic salts, and their effects on enzyme recovery are different from those of water-soluble inorganic salts. In water-soluble inorganic salts, the ionic size (molecular weight) upon dissociation of each salt is smaller than in organic salts, and this is thought to result in high recovery of enzyme in the later-described Step (2).

The water-soluble inorganic salt(s) is/are not restricted, and a salt(s) selected from the group consisting of sodium salts, potassium salts, magnesium salts, calcium salts and ammonium salts may be preferably used. Among these, a salt(s) selected from the group consisting of sodium chloride, sodium sulfate, magnesium chloride, magnesium sulfate, potassium chloride, calcium chloride and ammonium sulfate is/are preferably used since their raw material costs are low and high enzyme recovery can be obtained therewith. Further, monovalent inorganic salts such as sodium chloride and potassium chloride have an advantage in that their combination with nanofiltration membrane treatment at a later stage allows removal of a sufficient amount of the salts. Ammonium sulfate is not removed by a nanofiltration membrane, but in cases where the sugar liquid is used as a fermentation feedstock for a microorganism, ammonium sulfate is used as a nitrogen source for the growth of the microorganism. Therefore, ammonium sulfate is preferably used as the water-soluble inorganic salt. Either a single type or a plurality of types of water-soluble inorganic salt(s) may be added. For example, hydrolysis in the presence of 2.1 g/L sodium chloride, 0.2 g/L magnesium chloride and 2.7 g/L ammonium sulfate corresponds to addition of the inorganic salts at a total concentration of 5 g/L (=2.1+0.2+2.7) in the hydrolysis.

Addition of the water-soluble inorganic salt(s) may be carried out either before addition of the filamentous fungus-derived cellulase or after addition of the filamentous fungus-derived cellulase to the pretreated product of cellulose. However, addition of the inorganic salt(s) before addition of the filamentous fungus-derived cellulase is preferred since in this case, for example, contamination with microorganisms and a decrease in the yield of produced sugar caused thereby can be suppressed during hydrolysis of the pretreated product of biomass with the filamentous fungus-derived cellulase.

Although the water-soluble inorganic salt(s) may be added in the form of either a solid such as a powder, or an aqueous solution, a method wherein a concentrated aqueous inorganic salt solution at a concentration of about 5 to 500 g/L is preliminarily prepared and the prepared solution is added when the hydrolysis is carried out is preferred. Addition of an inorganic salt in the solid state locally causes extreme elevation of the inorganic salt concentration, and hence inactivation of the filamentous fungus-derived cellulase may occur. Also in view of operability, an aqueous solution is preferred.

The water-soluble inorganic salt(s) may be added such that the final concentration of the water-soluble inorganic salt(s) is 5 to 35 g/L. The pretreated product of cellulose contains inorganic salts (salts of phosphorus, sodium, potassium and the like) that are derived from the original cellulose biomass and/or from the pretreatment. In a known method of measuring inorganic substances such as inorganic salts originally contained in cellulose biomass, the ash content is measured; that is, a biomass combustion test is carried out in the presence of air at 815° C. and the constant weight of the obtained solid residue is measured to measure the inorganic substances. The ash content derived from the cellulose biomass as measured by this method is less than about 3% by weight with respect to the biomass weight. However, the ash content is mostly silica (Si). Such silica compounds have extremely low water solubility and are therefore not water-soluble inorganic salts. When a pretreated product of cellulose is hydrolyzed with cellulase, the solid concentration is adjusted to 50 to 250 g/L, and, even if the whole ash content derived from the biomass is composed of water-soluble inorganic salts, the concentration of the water-soluble inorganic salts during hydrolysis is 1.5 to 3 g/L. Thus, it can be said that the hydrolysis is carried out in the presence of water-soluble inorganic salts within a remarkably high final concentration range as compared to cases of hydrolysis with a normal pretreated product of cellulose.

The amount of the water-soluble inorganic salt(s) added and the final concentration of the water-soluble inorganic salt(s) may be measured by ion chromatography. In the hydrolysis of the pretreated product of cellulose, a certain level of increase in the concentration of the water-soluble inorganic salt(s) may occur, but the amount of the water-soluble inorganic salt(s) to be added may be determined by measuring the final concentration of the water-soluble inorganic salt(s) before feeding the enzyme.

Each water-soluble inorganic salt is preferably a reagent-grade water-soluble inorganic salt but, for example, a water-soluble inorganic salt derived from sea water, or a water-soluble inorganic salt derived from the ash content obtained after combustion of a cellulose-containing biomass, may also be used as an alternative.

Water-soluble inorganic salts contained in sea water are known to have various concentrations depending on the place where the sea water was collected, but, in general, they constitute a mixture of water-soluble inorganic salts with a composition of 24 to 27 g/L sodium chloride, 2.5 to 4 g/L magnesium chloride, 1 to 2.5 g/L magnesium sulfate and about 0.7 g/L potassium chloride. The pH of sea water mostly depends on the salt composition, and is generally pH 8.2 to 8.5. Therefore, sea water may be used as the water-soluble inorganic salts after adjustment of its pH to a value most appropriate for hydrolysis with filamentous fungus-derived cellulase. In particular, in cases where *Trichoderma*-derived cellulase is used as the filamentous fungus-derived cellulase, the pH is preferably adjusted to 4 to 6 since a pH outside this range may cause inactivation of the enzyme. For adjustment of the pH, a commonly used acid such as sulfuric acid or hydrochloric acid may be used, and the type of the acid is not limited.

Further, an ash content obtained by boiler combustion of a cellulose-containing biomass, of a pretreated product of the biomass, or of a saccharification residue obtained after hydrolysis of the biomass, may be used as an alternative to the water-soluble inorganic salt(s). Such an ash content contains a large amount of potassium, and, by dissolving the ash content in water and adjusting the pH, an aqueous solution of water-soluble inorganic salts can be prepared. Dissolution of the ash content in water results in an alkaline pH. This is because potassium forms potassium hydroxide, and, by its neutralization with sulfuric acid or hydrochloric acid, potassium chloride or potassium sulfate as a water-soluble inorganic salt is formed. Further, the ash content contains a large amount of water-insoluble silica, and such a water-insoluble inorganic substance is preferably removed by an appropriate method such as filtration.

Further, after neutralizing the acid or alkali used in the pretreatment of cellulose-containing biomass, a water-soluble inorganic salt(s) produced by the neutralization may be used. For example, in cases where an aqueous solution of sodium hydroxide, ammonia or the like is used in the pretreatment of cellulose-containing biomass, an aqueous solution of sodium hydroxide or ammonia may remain in the pretreated product of cellulose (solid) obtained by solid-liquid separation after the pretreatment. By neutralizing the alkali remaining in the pretreated product of cellulose (solid) using sulfuric acid or the like, an inorganic salt such as sodium sulfate, ammonium sulfate or the like can be produced as a result of the neutralization. That is, the reagent actually "added" is an alkali, but its neutralization produces a required amount of a water-soluble inorganic salt. The "adding a water-soluble inorganic salt(s)" also includes cases where the final concentration of the water-soluble inorganic salt(s) is adjusted to 5 to 35 g/L by such a step of hydrolysis using filamentous fungus-derived cellulase wherein an acid is added. Similarly, in cases where sulfuric acid is used in the pretreatment of cellulose-containing biomass, use of ammonia or sodium hydroxide for its neutralization allows production of a water-soluble inorganic salt, that is, ammonium sulfate or sodium sulfate (FIG. 1).

Figure 2:
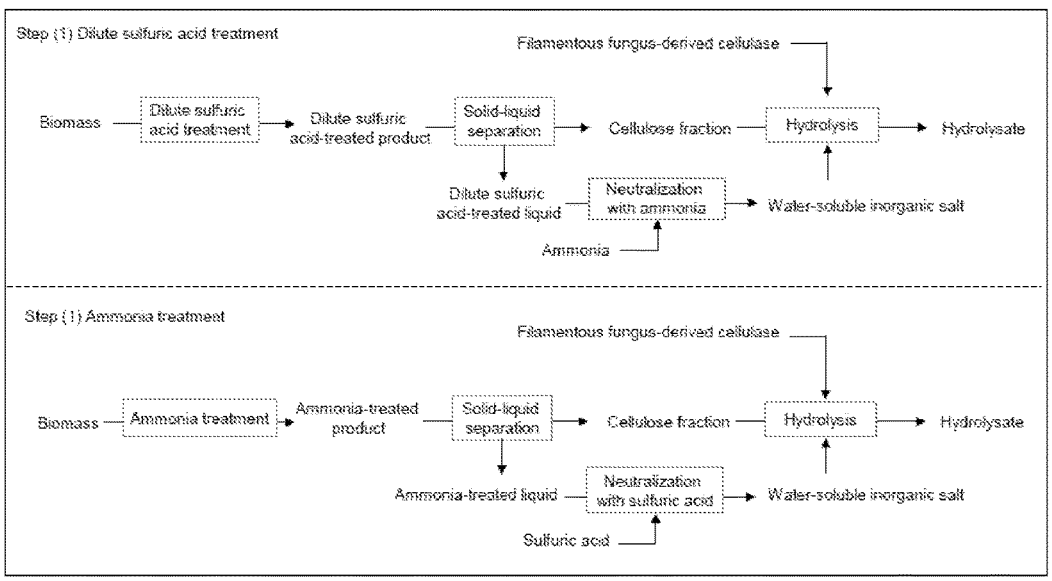
FIG. 2 is a schematic flow diagram showing an example of Step (1) of our method. That is.

Further, the water-soluble inorganic salt to be used may also be obtained by neutralizing: a solution component prepared by pretreating a cellulose-containing biomass with an acid or alkali and then subjecting the resultant to solid-liquid separation for separation into a pretreated product of cellulose (solid) and the solution component; or a solution component obtained by washing a pretreated product of cellulose (solid) with water or the like. Of course, the "adding a water-soluble inorganic salt(s)" also includes cases where the inorganic salt(s) prepared by neutralization is/are made to be contained in the pretreated product of cellulose (solid) at a final concentration of 5 to 35 g/L (FIG. 2).

Table 1 summarizes combinations of the pretreatment and the neutralizer in the above cases where a water-soluble inorganic salt is produced by neutralization.

TABLE 1

Combinations of pretreatment and a neutralizer in preparation examples of water-soluble inorganic salts

| Pretreatment | Neutralizer | Water-soluble inorganic salt |
| --- | --- | --- |
| Ammonia treatment | Sulfuric acid | Ammonium sulfate |
| | Hydrochloric acid | Ammonium chloride |
| | Acetic acid | Ammonium acetate |
| Sodium hydroxide treatment | Sulfuric acid | Sodium sulfate |
| | Hydrochloric acid | Sodium chloride |
| | Acetic acid | Sodium acetate |
| Sulfuric acid treatment | Ammonia | Ammonium sulfate |
| | Sodium hydroxide | Sodium sulfate |
| | Potassium hydroxide | Potassium sulfate |

On the other hand, for example, our method does not include cases where calcium hydroxide (lime) is used as a neutralizer to produce calcium sulfate as an inorganic salt since calcium hydroxide is not a water-soluble inorganic salt.

The addition of a water-soluble inorganic salt(s) in Step (1) not only has an effect to increase the recovery of filamentous fungus-derived cellulase in Step (2) described below, but also enables suppression of contamination with microorganisms in the hydrolysis step and a decrease in the yield of sugar caused thereby. When a filamentous fungus-derived cellulase is used in the hydrolysis, the reaction temperature is 40 to 60° C., but this temperature range corresponds optimal culture temperatures for microorganisms such as lactic acid bacteria including *Bacillus*, and heat-tolerant yeasts, contained in the treated product. Therefore, such microorganisms may consume the produced sugar. By addition of the water-soluble inorganic salt(s) in Step (1), loss of the produced sugar due to contamination with such microorganisms can be largely suppressed. That is, addition of the water-soluble inorganic salt(s) not only has an effect to improve the enzyme recovery, but also has an effect to improve the sugar yield.

In Step (1), the pretreated product of cellulose described above is subjected to hydrolysis with a filamentous fungus-derived cellulase to obtain a hydrolysate. The hydrolysis of cellulose means to decrease the molecular weight of cellulose. Further, in the hydrolysis of cellulose, hemicellulose components such as xylan, mannan and arabinan are hydrolyzed at the same time. Examples of monosaccharide components contained in the hydrolysate include glucose, xylose, mannose and galactose, and the major monosaccharide component is glucose, which is a hydrolysate of cellulose. Further, in cases where the hydrolysis is insufficient, disaccharides such as cellobiose and xylobiose; cello-oligosaccharides; and xylo-oligosaccharides; are contained.

In Step (1), the pretreated product of cellulose is hydrolyzed with a filamentous fungus-derived cellulase. Specific examples of the filamentous fungus include *Trichoderma, Aspergillus, Cellulomonas, Clostridium, Streptomyces, Humicola, Acremonium, Irpex, Mucor, Talaromyces, Phanerochaete*, white-rot fungi and brown-rot fungi. Among such filamentous fungus-derived cellulases, *Trichoderma*-derived cellulase, which has high cellulose-degrading activity, is preferably used.

The *Trichoderma*-derived cellulase is an enzyme composition comprising cellulase derived from a microorganism belonging to the genus *Trichoderma* as a major component. The microorganism belonging to the genus Trichoderma is not restricted, and specific examples of such a microorganism include *Trichoderma reesei* QM9414, *Trichoderma reesei* QM9123, *Trichoderma reesei* Rut C-30, *Trichoderma reesei* PC3-7, *Trichoderma reesei* ATCC68589, *Trichoderma reesei* CL-847, *Trichoderma reesei* MCG77, *Trichoderma reesei* MCG80 and *Trichoderma viride* QM9123 (*Trichoderma viride* 9123). The cellulase may also be derived from a mutant strain originated from the above-described *Trichoderma* microorganism, which mutant strain was prepared by mutagenesis using a mutagen, UV irradiation or the like to enhance the cellulase productivity.

The *Trichoderma*-derived cellulase is an enzyme composition that comprises a plurality of enzyme components such as cellobiohydrolase, endoglucanase, exoglucanase, β-glucosidase, xylanase and xylosidase, which enzyme composition has an activity to hydrolyze cellulose to cause saccharification. In cellulose degradation, *Trichoderma*-derived cellulase has a coordinate effect or complementary effect by the plurality of enzyme components, and enables more efficient hydrolysis of cellulose thereby. The cellulase especially preferably comprises *Trichoderma*-derived cellobiohydrolase and xylanase.

Cellobiohydrolase is a general term for cellulases that hydrolyze cellulose from the terminal portions. The group of enzymes belonging to cellobiohydrolase are described as EC number: EC3.2.1.91.

Endoglucanase is a general term for cellulases that hydrolyze cellulose molecular chains from their central portions. The group of enzymes belonging to endoglucanase are described as EC numbers: EC3.2.1.4, EC3.2.1.6, EC3.2.1.39 and EC3.2.1.73.

Exoglucanase is a general term for cellulases that hydrolyze cellulose molecular chains from their termini. The group of enzymes belonging to exoglucanase are described as EC numbers: EC3.2.1.74 and EC3.2.1.58.

β-glucosidase is a general term for cellulases that act on cello-oligosaccharides or cellobiose. The group of enzymes belonging to β-glucosidase are described as EC number: EC3.2.1.21.

Xylanase is a general term for cellulases that act on hemicellulose or, especially, xylan. The group of enzymes belonging to xylanase are described as EC number: EC3.2.1.8.

Xylosidase is a general term for cellulases that act on xylo-oligosaccharides. The group of enzymes belonging to xylosidase are described as EC number: EC3.2.1.37.

As the *Trichoderma*-derived cellulase, a crude enzyme product is preferably used. The crude enzyme product is derived from a culture supernatant obtained by culturing a *Trichoderma* microorganism for an arbitrary period in a medium prepared such that the microorganism produces cellulase. The medium components to be used are not restricted, and a medium supplemented with cellulose to promote production of cellulase may be generally used. As the crude enzyme product, the culture liquid may be used as it is, or the culture supernatant processed only by removal of *Trichoderma* cells may be preferably used.

The weight ratios of enzyme components in the crude enzyme product are not restricted and, for example, a culture liquid derived from *Trichoderma reesei* contains 50 to 95% by weight cellobiohydrolase, and also contains as other components endoglucanase, β-glucosidase and the like. Microorganisms belonging to *Trichoderma* produce strong cellulase components into the culture liquid, while the β-glucosidase activity in the culture liquid is low since β-glucosidase is retained in the cells or on the cell surfaces. Therefore, β-glucosidase from a different species or from the same species may be added to the crude enzyme product. As the 62-glucosidase from a different species, β-glucosidase derived from *Aspergillus* may be preferably used. Examples of the β-glucosidase derived from *Aspergillus* include "Novozyme 188," which is commercially available from Novozyme. The method of addition of β-glucosidase from a different species or from the same species to the crude enzyme product may also be a method wherein a gene is introduced to a microorganism belonging to *Trichoderma* to perform genetic recombination of the microorganism such that β-glucosidase is produced into the culture liquid, and the microorganism belonging to *Trichoderma* is then cultured, followed by isolating the culture liquid.

The reaction temperature for hydrolysis with the filamentous fungus-derived cellulase is preferably 15 to 100° C., more preferably 40 to 60° C., most preferably 50° C. The pH for the hydrolysis reaction is preferably pH 3 to 9, more preferably pH 4 to 5.5, most preferably pH 5. To adjust the pH, an acid or alkali may be added such that a desired pH is achieved. Further, as required, a buffer may be used.

In addition, in the hydrolysis of a pretreated product of cellulose, stirring/mixing is preferably carried out to promote contacting between the pretreated product of cellulose and the filamentous fungus-derived cellulase, and to achieve a uniform sugar concentration in the hydrolysate. The solid concentration of the pretreated product of cellulose is more preferably 1 to 25% by weight. Further, setting the solid concentration to a low concentration of 1 to 10% by weight is still more preferred since this has an effect to improve the efficiency of hydrolysis of the pretreated product of cellulose. This effect is due to the property of the filamentous fungus-derived cellulase that the enzyme reaction is inhibited by sugar products such as glucose and cellobiose, which are products by the hydrolysis.

Step (2)

In Step (2), the hydrolysate obtained in Step (1) is subjected to solid-liquid separation, and the solution component is recovered. The solid-liquid separation can be carried out by a known solid-liquid separation method such as centrifugation using a screw decanter or the like; filtration including pressure/suction filtration; or membrane filtration including microfiltration. Such solid-liquid separation may also be carried out as a combination of more than one method, and is not restricted as long as solids can be efficiently removed thereby. However, in view of suppression of fouling of an ultrafiltration membrane at a later stage, the solution component after the solid-liquid separation is preferably solid-free as much as possible and, more specifically, it is preferred to carry out first solid-liquid separation by centrifugation or by filtration using a filter press or the like, followed by further subjecting the obtained solution component to membrane filtration through a microfiltration membrane to completely remove solids. A microfiltration membrane is also called membrane filter, and is a separation membrane that can separate and remove particles having sizes of about 0.01 to 10 μm from a particulate suspension using a pressure difference as a driving force. A microfiltration membrane has pores having a size of 0.01 to 10 μm on its surface, and particulate components larger than the pores can be separated/removed to the membrane side. Examples of the material of a microfiltration membrane include, but are not limited to, cellulose acetate, aromatic polyamide, polyvinyl alcohol, polysulfone, polyvinylidene fluoride, polyethylene, polyacrylonitrile, ceramic, polypropylene, polycarbonate and polytetrafluoroethylene (Teflon (registered trademark)). The membrane is preferably a polyvinylidene fluoride microfiltration membrane in view of contamination resistance, chemical resistance, strength, filtration performance and the like.

Subsequently, the solution component is subjected to ultrafiltration membrane treatment. An ultrafiltration membrane generally means a separation membrane that has a pore size of 1.5 nanometers to 250 nanometers and can block water-soluble macromolecules having molecular weights of 1,000 to 200,000 as a non-permeate. The molecular weight cut off of the ultrafiltration membrane is not limited as long as filamentous fungus-derived cellulase can be recovered, and the molecular weight cut off is preferably 1,000 to 100,000 Da, more preferably 10,000 to 30,000 Da. Examples of the material of the ultrafiltration membrane that may be used include polyether sulfone (PES), polyvinylidene fluoride (PVDF) and regenerated cellulose, and, since cellulose is degraded by filamentous fungus-derived cellulase, the material of the ultrafiltration membrane is preferably a synthetic polymer such as PES or PVDF. Preferred examples of the shape of the ultrafiltration membrane include a tubular type, spiral element and flat membrane. Examples of the mode of filtration through the ultrafiltration membrane include cross-flow filtration and dead-end filtration, and, in view of fouling and the flux, cross-flow filtration is preferred.

By filtering the solution component through the ultrafiltration membrane, a sugar liquid can be obtained as a permeate. The sugar liquid obtained is a liquid produced by almost complete removal of the solids that have been originally contained in the sugar liquid by solid-liquid separation. On the other hand, by filtration through the ultrafiltration membrane, colored substances and water-soluble macromolecules are removed into the non-permeate side, and the water-soluble macromolecules contain the filamentous fungus-derived cellulase component used in Step (1). The filamentous fungus-derived cellulase component to be recovered is not limited, and the whole or a part of the filamentous fungus-derived cellulase component used in the hydrolysis can be recovered as a non-permeate. Since the non-permeate also contains sugar components derived from the sugar liquid, an operation of adding water to the non-permeate and further filtering the resultant through an ultrafiltration membrane may be repeated for recovering such sugar components.

Step (2) has an effect to remarkably increase the enzyme amount of filamentous fungus-derived cellulase contained in the recovered enzyme as compared to conventional techniques and, among the filamentous fungus-derived cellulase components, cellobiohydrolase and xylanase are recovered especially at high efficiency. By reusing the recovered filamentous fungus-derived cellulase for hydrolysis of the pretreated product of cellulose, the amount of the filamentous fungus-derived cellulase used can be reduced. The recovered filamentous fungus-derived cellulase may be reused alone for the hydrolysis, or may be reused after being mixed with fresh filamentous fungus-derived cellulase. Further, in some cases, the recovered filamentous fungus-derived cellulase may be effectively utilized in a use other than hydrolysis of cellulose.

By filtering, as in the method described in WO 2010/067785, the sugar liquid obtained in Step (2) through a nanofiltration membrane and/or reverse osmosis membrane, a sugar concentrate containing concentrated sugar components can be obtained as a non-permeate.

A nanofiltration membrane is also called a nanofilter (nanofiltration membrane, NF membrane), and generally defined as a "membrane that allows permeation of monovalent ions, but blocks divalent ions." The membrane is considered to have fine voids having sizes of about several nanometers, and mainly used to block fine particles, molecules, ions, salts and the like in water.

A reverse osmosis membrane is also called an RO membrane, and generally defined as a "membrane having a desalting function also for monovalent ions." The membrane is considered to have ultrafine voids having sizes of about several angstroms to several nanometers, and mainly used for removal of ion components such as seawater desalination and ultrapure water production.

Examples of the material of the nanofiltration membrane or reverse osmosis membrane that may be used include polymer materials such as cellulose acetate polymers, polyamides, polyesters, polyimides, vinyl polymers and polysulfones. The membrane is not limited to a membrane constituted by one of the materials, and may be a membrane comprising a plurality of the membrane materials.

As the nanofiltration membrane to be used, a spiral-wound membrane element is preferred. Specific examples of preferred nanofiltration membrane elements include a cellulose acetate nanofiltration membrane element "GE Sepa," manufactured by GE Osmonics; nanofiltration membrane elements NF99 and NF99HF, manufactured by Alfa-Laval, which have polyamide functional layers; nanofiltration membrane elements NF-45, NF-90, NF-200, NF-270 and NF-400, manufactured by FilmTec Corporation, which have cross-linked piperazine polyamide functional layers; and nanofiltration membrane elements SU-210, SU-220, SU-600 and SU-610, manufactured by Toray Industries, Inc., comprising a nanofiltration membrane UTC60, manufactured by the same manufacturer, which comprises a cross-linked piperazine polyamide as a major component. The nanofiltration membrane element is more preferably NF99 or NF99HF; NF-45, NF-90, NF-200 or NF-400; or SU-210, SU-220, SU-600 or SU-610. The nanofiltration membrane element is still more preferably SU-210, SU-220, SU-600 or SU-610.

In terms of the material of the reverse osmosis membrane, examples of the membrane include a composite membrane comprising a cellulose acetate polymer as a functional layer (hereinafter referred to as cellulose acetate reverse osmosis membrane) and a composite membrane comprising a polyamide as a functional layer (hereinafter referred to as polyamide reverse osmosis membrane). Examples of the cellulose acetate polymer herein include polymers prepared with organic acid esters of cellulose such as cellulose acetate, cellulose diacetate, cellulose triacetate, cellulose propionate and cellulose butyrate, which may be used alone, as a mixture, or as a mixed ester. Examples of the polyamide include linear polymers and cross-linked polymers constituted by aliphatic and/or aromatic diamine monomers.

Specific examples of the reverse osmosis membrane include polyamide reverse osmosis membrane modules manufactured by TORAY INDUSTRIES, INC., SUL-G10 and SUL-G20, which are ultralow-pressure type modules, and SU-710, SU-720, SU-720F, SU-710L, SU-720L, SU-720LF, SU-720R, SU-710P and SU-720P, which are low-pressure type modules, as well as SU-810, SU-820, SU-820L and SU-820FA, which are high-pressure type modules containing UTC80 as a reverse osmosis membrane; cellulose acetate reverse osmosis membranes manufactured by the same manufacturer, SC-L100R, SC-L200R, SC-1100, SC-1200, SC-2100, SC-2200, SC-3100, SC-3200, SC-8100 and SC-8200; NTR-759HR, NTR-729HF, NTR-70SWC, ES10-D, ES20-D, ES20-U, ES15-D, ES15-U and LF10-D, manufactured by Nitto Denko Corporation; RO98pHt, R099, HR98PP and CE4040C-30D, manufactured by Alfa-Laval; GE Sepa, manufactured by GE; BW30-4040, TW30-4040, XLE-4040, LP-4040, LE-4040, SW30-4040 and SW3OHRLE-4040, manufactured by FilmTec Corporation; TFC-HR and TFC-ULP, manufactured by KOCH; and ACM-1, ACM-2 and ACM-4, manufactured by TRISEP.

Concentrating the sugar liquid using a nanofiltration membrane and/or reverse osmosis membrane has an advantage that the sugar concentration in the sugar liquid can be increased and fermentation inhibitors can be removed as a permeate. The term "fermentation inhibitors" herein means components, other than sugars, that inhibit fermentation in the fermentation step at a later stage, and specific examples of the fermentation inhibitors include aromatic compounds, furan compounds, organic acids and monovalent inorganic salts. Representative examples of such aromatic compounds and furan compounds include furfural, hydroxymethylfurfural, vanillin, vanillic acid, syringic acid, coniferyl aldehyde, coumaric acid and ferulic acid. Examples of organic acids include acetic acid and formic acid. The sugar concentration in the sugar concentrate may be arbitrary set within the range of 50 to 400 g/L depending on the treatment conditions for the nanofiltration membrane and/or the reverse osmosis membrane, and may be arbitrary set depending on the use of the sugar concentrate and/or the like. In cases where more complete removal of fermentation inhibitors is required, water may be added to the sugar liquid or the sugar concentrate, followed by concentrating the resultant through a nanofiltration membrane and/or a reverse osmosis membrane to a desired sugar concentration. By this, fermentation inhibitors can be removed as a permeate. Use of a nanofiltration membrane is more preferred since it has higher effect of removing fermentation inhibitors than a reverse osmosis membrane. Whether to use a nanofiltration membrane or to use a reverse osmosis membrane may be selected in consideration of the concentration of fermentation inhibitors contained in the sugar liquid, or of how the fermentation at a later stage is influenced by the fermentation inhibitors.

In cases where a sugar concentrate is obtained by passing a sugar liquid through a nanofiltration membrane, the permeate of the nanofiltration membrane may be further filtered through a reverse osmosis membrane to obtain an inorganic salt concentrate as a non-permeate. The inorganic salt concentrate comprises the water-soluble inorganic salt(s) added in Step (1) as a major component, and can be preferably reused in Step (1).

Use of Sugar Liquid

By using a sugar liquid as a fermentation feedstock to grow microorganisms having capacity to produce chemical products, various chemicals can be produced. "Growing microorganisms using a sugar liquid as a fermentation feedstock" herein means that sugar components or amino sources contained in the sugar liquid are used as nutrients for microorganisms, to cause, and to allow continuation of, growth of the microorganisms. Specific examples of the chemical products include alcohols, organic acids, amino acids and nucleic acids, which are substances mass-produced in the fermentation industry. Such chemical products are produced and accumulated inside and outside the living body by using sugar components in the sugar liquid as carbon sources to be metabolized. Specific examples the chemical products that can be produced by microorganisms include alcohols such as ethanol, 1,3-propanediol, 1,4-propanediol and glycerol; organic acids such as acetic acid, lactic acid, pyruvic acid, succinic acid, malic acid, itaconic acid and citric acid; nucleosides such as inosine and guanosine; nucleotides such as inosinic acid and guanylic acid; and amine compounds such as cadaverine. Further, the sugar liquid can be applied to production of enzymes, antibiotics, recombinant proteins and the like. The microorganism used for production of such a chemical product is not limited as long as the microorganism is capable of efficiently producing the chemical product of interest, and examples of the microorganism that may be used include microorganisms such as *E. coli*, yeasts, filamentous fungi and Basidiomycetes.

Apparatus Constitution

Figure 3:
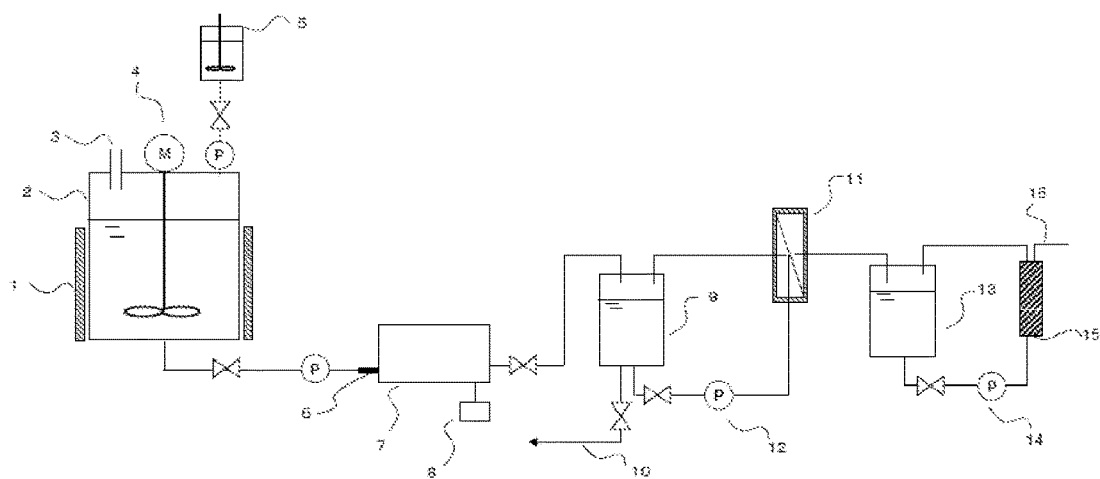
FIG. 3 is a diagram showing an example of a device constitution that carries out our method of producing a sugar liquid.

An example of the constitution of the apparatus for carrying out the method of producing a sugar liquid is shown in FIG. 3. A hydrolysis tank (2) is for hydrolysis of a pretreated product of cellulose, and comprises an incubator (1) that enables incubation at a temperature of 40° C. to 60° C., an inlet (3) through which a pretreated product of cellulose is fed, a stirrer (4) for mixing the pretreated product of cellulose, and a water-soluble-inorganic-salt preparation tank (5) for preparing, retaining and adding a water-soluble inorganic salt(s). A press filtration (7) wherein solid-liquid separation of a hydrolysate is carried out comprises an inlet (6) for the hydrolysate and a compressor (8). The filtrate after press filtration is collected into a press filtration filtrate tank (9). The press filtration filtrate tank (9) is connected via an MF pump (12) to a microfiltration membrane (11). Solids separated by the microfiltration membrane (11) are concentrated in the press filtrate tank (9) and discharged through a discharge line (10). The filtrate from the microfiltration membrane is collected into a microfiltration membrane filtrate tank (13). The microfiltration membrane filtrate tank is connected via a UF pump (14) to an ultrafiltration membrane (15) by which filamentous fungus-derived cellulase can be separated/recovered as a non-permeate. A sugar liquid is recovered through a sugar liquid collection line (16), as a filtrate of the ultrafiltration membrane (15).

EXAMPLES

Our methods are described below more specifically by way of Examples. However, this disclosure is not limited to these.

Reference Example 1

Preparation of Pretreated Product of Cellulose
1) Preparation of Pretreated Product of Cellulose 1 (Ammonia Treatment)

As a cellulose, rice straw was used. The cellulose was fed to a small reactor (manufactured by Taiatsu Techno Corporation, TVS-N2 30 ml), and cooled in liquid nitrogen. Ammonia gas was flown into this reactor, and the sample was completely immersed in liquid ammonia. The lid of the reactor was closed, and the reactor was left to stand at room temperature for about 15 minutes. Subsequently, the reactor was processed in an oil bath at 150° C. for 1 hour. Thereafter, the reactor was removed from the oil bath, and the ammonia gas was leaked in a fume hood, followed by vacuuming the inside of the reactor to 10 Pa with a vacuum pump, thereby drying the cellulose. The resultant was used in the Examples below as a pretreated product of cellulose 1.

2) Preparation of Pretreated Product of Cellulose 2 (Hydrothermal Treatment)

As the cellulose, rice straw was used. The cellulose was immersed in water, and subjected to treatment using an autoclave (manufactured by Nitto Koatsu Co., Ltd.) with stirring at 180° C. for 20 minutes with stirring. The treatment was carried out at a pressure of 10 MPa. After the treatment, solid-liquid separation was carried out by centrifugation (3000 G) to separate the solid component from the solution component (hereinafter referred to as "hydrothermally treated liquid"). The solid component was used in the Examples below as a pretreated product of cellulose 2.

Reference Example 2

Measurement of Sugar Concentration

The concentrations of glucose and xylose contained in the sugar liquid were measured under the HPLC conditions described below based on comparison with standard samples:

Column: Luna $NH_2$ (manufactured by Phenomenex, Inc.)
Mobile phase: MilliQ:acetonitrile=25:75 (flow rate, 0.6 mL/minute)
Reaction solution: None
Detection method: RI (differential refractive index)
Temperature: 30° C.

Reference Example 3

Preparation of *Trichoderma*-derived Cellulase

*Trichoderma*-derived cellulase was prepared by the method described below.

Preculture

The mixture of 5% (w/vol) corn steep liquor, 2% (w/vol) glucose, 0.37% (w/vol) ammonium tartrate, 0.14% (w/vol) ammonium sulfate, 0.2% (w/vol) potassium dihydrogen phosphate, 0.03% (w/vol) calcium chloride dihydrate, 0.03% (w/vol) magnesium sulfate heptahydrate, 0.02% (w/vol) zinc chloride, 0.01% (w/vol) iron (III) chloride hexahydrate, 0.004% (w/vol) copper (II) sulfate pentahydrate, 0.0008% (w/vol) manganese chloride tetrahydrate, 0.0006% (w/vol) boric acid and 0.0026% (w/vol) hexaammonium heptamolybdate tetrahydrate in distilled water was prepared, and 100 mL of this mixture was placed in a baffled 500-mL Erlenmeyer flask, followed by being sterilized by autoclaving at 121° C. for 15 minutes. After allowing the mixture to cool, PE-M and Tween 80, each of which was sterilized by autoclaving at 121° C. for 15 minutes separately from the mixture, were added thereto at 0.01% (w/vol) each. To this preculture medium, *Trichoderma reesei* ATCC68589 was inoculated at 1×10$^5$ cells/mL, and the cells were cultured at 28° C. for 72 hours with shaking at 180 rpm, to perform preculture (shaker: BIO-SHAKER BR-40LF, manufactured by TAITEC CORPORATION).

Main Culture

The mixture of 5% (w/vol) corn steep liquor, 2% (w/vol) glucose, 10% (w/vol) cellulose (Avicel), 0.37% (w/vol) ammonium tartrate, 0.14% (w/vol) ammonium sulfate, 0.2% (w/vol) potassium dihydrogen phosphate, 0.03% (w/vol) calcium chloride dihydrate, 0.03% (w/vol) magnesium sulfate heptahydrate, 0.02% (w/vol) zinc chloride, 0.01% (w/vol) iron (III) chloride hexahydrate, 0.004% (w/vol) copper (II) sulfate pentahydrate, 0.0008% (w/vol) manganese chloride tetrahydrate, 0.0006% (w/vol) boric acid and 0.0026% (w/vol) hexaammonium heptamolybdate tetrahydrate in distilled water was prepared, and 2.5 L of this mixture was placed in a 5-L stirring jar (manufactured by ABLE, DPC-2A), followed by being sterilized by autoclaving at 121° C. for 15 minutes. After allowing the mixture to cool, PE-M and Tween 80, each of which was sterilized by autoclaving at 121° C. for 15 minutes separately from the mixture, were added thereto at 0.1% each. To the resulting mixture, 250 mL of a preculture of *Trichoderma reesei* ATCC68589 preliminarily prepared with a liquid medium by the method described above was inoculated. The cells were then cultured at 28° C. for 87 hours at 300 rpm at an aeration rate of 1 vvm. After centrifugation, the supernatant was subjected to membrane filtration (Stericup-GV, manufactured by Millipore, material: PVDF). To the culture liquid prepared under the above-described conditions, β-glucosidase (Novozyme 188) was added at a protein weight ratio of 1/100, and the resulting mixture was used as *Trichoderma*-derived cellulase in the Examples below.

Reference Example 4

Method for Measuring Amount of Recovery of Filamentous Fungus-derived Cellulase

The amount of the filamentous fungus-derived cellulase that can be recovered in Step (2) was quantified by measuring 3 kinds of degradation activities (hereinafter referred to as activity values): 1) crystalline cellulose-degrading activity; 2) cellobiose-degrading activity; and 3) xylan-degrading activity.

1) Crystalline Cellulose-degrading Activity

To an enzyme liquid, a crystalline cellulose Avicel (Cellulose Microcrystalline, manufactured by Merck) was added at 1 g/L and sodium acetate buffer (pH 5.0) was added at 100 mM, followed by allowing the resulting mixture to react at 50° C. for 24 hours. This reaction liquid was prepared in a 1-mL tube, and the reaction was allowed to proceed with mixing by rotation under the above-described conditions. Thereafter, the tube was subjected to centrifugation, and the glucose concentration in the supernatant component was measured. The measurement of glucose concentration was carried out according to the method described in Reference Example 2. The concentration of glucose produced (g/L) was used as it is as the activity level of the crystalline cellulose-degrading activity, and used for comparison of the amount of enzyme recovered.

2) Cellobiose-degrading Activity

To an enzyme liquid, cellobiose (Wako Pure Chemical Industries, Ltd.) was added at 500 mg/L and sodium acetate buffer (pH 5.0) was added at 100 mM, followed by allowing the resulting mixture to react at 50° C. for 0.5 hour. This reaction liquid was prepared in a 1-mL tube, and the reaction was allowed to proceed with mixing by rotation under the above-described conditions. Thereafter, the tube was subjected to centrifugation, and the glucose concentration in the supernatant component was measured. The measurement of glucose concentration was carried out according to the method described in Reference Example 2. The concentration of glucose produced (g/L) was used as it is as the activity level of the cellobiose-degrading activity, and used for comparison of the amount of enzyme recovered.

3) Xylan-degrading Activity

To an enzyme liquid, xylan (Birch wood xylan, manufactured by Wako Pure Chemical Industries, Ltd.) was added at 10 g/L and sodium acetate buffer (pH 5.0) was added at 100 mM, followed by allowing the resulting mixture to react at 50° C. for 4 hours. This reaction liquid was prepared in a 1-mL tube, and the reaction was allowed to proceed with mixing by rotation under the above-described conditions. Thereafter, the tube was subjected to centrifugation, and the xylose concentration in the supernatant component was measured. The measurement of xylose concentration was carried out according to the method described in Reference Example 2. The concentration of xylose produced (g/L) was used as it is as the activity level of the xylose-degrading activity, and used for comparison of the amount of enzyme recovered.

Reference Example 5

Measurement of Inorganic Ion Concentration

The concentrations of cations and anions contained in the sugar liquid were quantified under the HPLC conditions shown below by comparison with standard samples.

1) Cation Analysis
   Column: Ion Pac AS22 (manufactured by DIONEX)
   Mobile phase: 4.5 mM $Na_2CO_3$/1.4 mM $NaHCO_3$ (flow rate, 1.0 mL/minute)
   Reaction liquid: None
   Detection method: Electric conductivity (by use of a suppressor)
   Temperature: 30° C.

2) Anion Analysis
   Column: Ion Pac CS12A (manufactured by DIONEX)
   Mobile phase: 20 mM Methanesulfonic acid (flow rate, 1.0 mL/minute)
   Reaction liquid: None
   Detection method: Electric conductivity (by use of a suppressor)
   Temperature: 30° C.

Comparative Example 1

Hydrolysis of Pretreated Product of Cellulose

To the pretreated products of cellulose 1 and 2 (0.5 g each) prepared in Reference Example 1, distilled water was added, and 0.5 mL of the *Trichoderma*-derived cellulase prepared in Reference Example 3 was added, followed by further adding distilled water to a total weight of 10 g. Thereafter, dilute sulfuric acid or dilute caustic soda was added to the resulting composition such that the pH of the composition was within the range of 4.5 to 5.3. After the pH adjustment, the composition was transferred to a side-arm test tube (φ30

NS14/23, manufactured by Tokyo Rikakikai Co., Ltd.), and hydrolysis was carried out at 50° C. for 24 hours with incubation and stirring (compact mechanical stirrer CPS-1000, manufactured by Tokyo Rikakikai Co., Ltd., conversion adapter, feed inlet with a three-way stopcock, incubator MG-2200). The hydrolysate was subjected to solid-liquid separation by centrifugation (3000 G, 10 minutes), and thereby separated into the solution component (6 mL) and solids. Sugar concentrations (glucose and xylose concentrations) were measured according to the method described in Reference Example 2. The solution component was further filtered using a Millex HV filter unit (33 mm; made of PVDF; pore size, 0.45 µm). The obtained filtrate was filtered through an ultrafiltration membrane having a molecular weight cutoff of 10000 (VIVASPIN 20, manufactured by Sartorius stedim biotech, material: PES) and centrifuged at 4500 G until the membrane fraction was reduced to 1 mL. To the membrane fraction, 10 mL of distilled water was added, and the resulting mixture was centrifuged again at 4500 G until the membrane fraction was reduced to 1 mL. Thereafter, the enzyme was recovered from the membrane fraction. Activities of the recovered enzyme were measured according to Reference Example 4.

Comparative Example 2

Hydrolysis of Pretreated Product of Cellulose Containing Sodium Acetate (Organic Salt) 1

To the pretreated products of cellulose 1 and 2 (0.5 g each) prepared in Reference Example 1, distilled water was added, and 0.2 mL of 5 M sodium acetate (pH 5.2) (final concentration, 100 mM; 8.2 g/L) was further added, followed by addition of 0.5 mL of the *Trichoderma*-derived cellulase prepared in Reference Example 3 and then further addition of distilled water to a total weight of 10 g. The same operation as in Comparative Example 1 was carried out except for addition of the acetate buffer, and the sugar concentrations and each activity of the recovered enzyme were measured.

TABLE 2

Production of sugar/amount of enzyme recovered: pretreated product of cellulose 1

|  | Comparative Example 1 | Comparative Example 2 |
|---|---|---|
| Production of glucose (g/L) | 17 | 17 |
| Production of xylose (g/L) | 10 | 10 |
| Cellobiose-degrading activity | 2.3 | 2.3 |
| Crystalline cellulose-degrading activity | 0.22 | 0.22 |
| Xylan-degrading activity | 2.4 | 2.4 |

TABLE 3

Production of sugar/amount of enzyme recovered: pretreated product of cellulose 2

|  | Comparative Example 1 | Comparative Example 2 |
|---|---|---|
| Production of glucose (g/L) | 24 | 26 |
| Production of xylose (g/L) | 5 | 5 |
| Cellobiose-degrading activity | 1.2 | 1.2 |
| Crystalline cellulose-degrading activity | 0.1 | 0.1 |
| Xylan-degrading activity | 2.0 | 2.0 |

Example 1

Hydrolysis of Pretreated Product of Cellulose Supplemented with Water-soluble Inorganic Salt 1

Distilled water was added to the pretreated product of cellulose 1 (0.5 g) prepared in Reference Example 1, and a water-soluble inorganic salt (sodium chloride, potassium chloride, sodium sulfate, magnesium chloride, magnesium sulfate, calcium chloride or ammonium sulfate) was added thereto such that the final concentration the salt was 5 g/L, 10 g/L, 25 g/L, 35 g/L, 50 g/L or 100 g/L. To the resulting mixture, 0.5 mL of the *Trichoderma*-derived cellulase prepared in Reference Example 3 was added, and distilled water was further added thereto such that the total weight became 10 g. The same operation as in Comparative Example 1 was carried out except for addition of the acetate buffer, and the sugar concentrations and each activity of the recovered enzyme were measured.

The relationship between the amount of each water-soluble inorganic salt added and the sugar production is shown in Table 4 and Table 5. It was found that the amounts of glucose and xylose produced were the same as in Comparative Examples 1 and 2 (Tables 2 and 3) in the cases of addition of the water-soluble inorganic salt to a concentration of 35 g/L or less, but that their production decreased in the cases where the concentration was 50 g/L or higher. This is considered to be due to high concentration of the water-soluble inorganic salt, which caused inhibition of the enzyme reaction. On the other hand, no large decrease in the produced sugar was observed within the range of 5 to 35 g/L.

TABLE 4

| Production of glucose (g/L) | | | | | | |
|---|---|---|---|---|---|---|
|  | 5 g/L | 10 g/L | 25 g/L | 35 g/L | 50 g/L | 100 g/L |
| Sodium chloride | 17 | 17 | 16 | 16 | 14 | 5 |
| Sodium sulfate | 17 | 17 | 16 | 15 | 14 | 5 |
| Magnesium chloride | 17 | 17 | 16 | 14 | 14 | 5 |
| Calcium chloride | 17 | 17 | 16 | 15 | 14 | 5 |
| Ammonium sulfate | 17 | 17 | 16 | 15 | 14 | 5 |
| Potassium chloride | 17 | 17 | 16 | 16 | 14 | 5 |

TABLE 5

| Production of xylose (g/L) | | | | | | |
|---|---|---|---|---|---|---|
|  | 5 g/L | 10 g/L | 25 g/L | 35 g/L | 50 g/L | 100 g/L |
| Sodium chloride | 10 | 10 | 10 | 10 | 8 | 2 |
| Sodium sulfate | 10 | 10 | 10 | 10 | 8 | 2 |
| Magnesium chloride | 10 | 10 | 10 | 10 | 8 | 2 |
| Calcium chloride | 10 | 10 | 10 | 10 | 8 | 2 |
| Ammonium sulfate | 10 | 10 | 10 | 10 | 8 | 2 |
| Potassium chloride | 10 | 10 | 10 | 10 | 8 | 2 |

Tables 6 to 8 show results obtained by performing hydrolysis after addition of each water-soluble inorganic salt and then recovering the enzyme from the obtained solution component. It was revealed as shown in Tables 5 and 6 that the cellobiose-degrading activity and the xylan-degrading activity decreased at the water-soluble inorganic salt concentrations of not less than 50 g/L. On the other hand, as shown in Table 7, it was revealed that the xylan-degrading activity increased not less than 1.2-fold and the crystalline cellulose-degrading activity increased not less than 2-fold in the cases where the water-soluble inorganic salt concentration was 5 to 35 g/L. Further, although the cellobiose-degrading activity did not largely change at the water-soluble inorganic salt concentrations of 5 to 35 g/L, the activity was found to decrease when the water-soluble inorganic salt concentration was not less than 50 g/L.

TABLE 6

Cellobiose-degrading activity

|  | 5 g/L | 10 g/L | 25 g/L | 35 g/L | 50 g/L | 100 g/L |
|---|---|---|---|---|---|---|
| Sodium chloride | 2.3 | 2.7 | 3.2 | 3.1 | 2.1 | 1.0 |
| Magnesium sulfate | 2.5 | 2.8 | 3.5 | 2.8 | 2.1 | 1.0 |
| Magnesium chloride | 2.5 | 2.6 | 3.5 | 2.9 | 2.2 | 1.0 |
| Calcium chloride | 2.5 | 2.7 | 3.5 | 3.2 | 2.2 | 1.0 |
| Ammonium sulfate | 2.5 | 2.8 | 3.2 | 3.0 | 2.2 | 1.0 |
| Potassium chloride | 2.4 | 2.7 | 3.1 | 3.1 | 2.0 | 0.8 |

TABLE 7

Xylan-degrading activity

|  | 5 g/L | 10 g/L | 25 g/L | 35 g/L | 50 g/L | 100 g/L |
|---|---|---|---|---|---|---|
| Sodium chloride | 2.5 | 3.0 | 3.1 | 3.0 | 2.4 | 1.0 |
| Magnesium sulfate | 2.4 | 2.9 | 3.1 | 3.0 | 2.1 | 1.0 |
| Magnesium chloride | 2.6 | 2.7 | 3.0 | 3.0 | 2.4 | 1.0 |
| Calcium chloride | 2.5 | 2.6 | 3.1 | 3.1 | 2.1 | 1.0 |
| Ammonium sulfate | 2.6 | 3.2 | 3.5 | 3.2 | 2.5 | 1.0 |
| Potassium chloride | 2.5 | 2.8 | 2.8 | 3.1 | 2.1 | 0.8 |

TABLE 8

Crystalline cellulose-degrading activity

|  | 5 g/L | 10 g/L | 25 g/L | 35 g/L | 50 g/L | 100 g/L |
|---|---|---|---|---|---|---|
| Sodium chloride | 0.35 | 0.5 | 0.8 | 0.9 | 0.15 | 0.1 |
| Magnesium sulfate | 0.36 | 0.6 | 0.6 | 0.7 | 0.15 | 0.1 |
| Magnesium chloride | 0.38 | 0.62 | 0.62 | 0.5 | 0.15 | 0.1 |
| Calcium chloride | 0.35 | 0.45 | 0.45 | 0.7 | 0.15 | 0.1 |
| Ammonium sulfate | 0.7 | 1.0 | 0.69 | 0.6 | 0.15 | 0.1 |
| Potassium chloride | 0.4 | 0.4 | 0.5 | 0.5 | 0.1 | 0.1 |

Example 2

Hydrolysis of Pretreated Product of Cellulose Supplemented with Water-soluble Inorganic Salt 2

Distilled water was similarly added to the pretreated product of cellulose 2 (0.5 g), and hydrolysis was carried out by the same procedure as in Example 1. The concentrations of sugars obtained and each activity of the recovered enzyme were measured. The relationship between the amount of each water-soluble inorganic salt added and the sugar production is shown in Table 9 and Table 10. It was found that the amounts of glucose and xylose produced were the same as in Comparative Examples 1 and 2 (Tables 2 and 3) in the cases of addition of the water-soluble inorganic salt to a concentration of 35 g/L or less, but that their production decreased in the cases where the concentration was 50 g/L or higher. This is considered to be due to high concentration of the water-soluble inorganic salt, which caused inhibition of the enzyme reaction. On the other hand, no large decrease in the produced sugar was observed at 5 to 35 g/L.

TABLE 9

Production of glucose (g/L)

|  | 5 g/L | 10 g/L | 25 g/L | 35 g/L | 50 g/L | 100 g/L |
|---|---|---|---|---|---|---|
| Sodium chloride | 24 | 24 | 24 | 24 | 16 | 3 |
| Sodium sulfate | 24 | 24 | 24 | 24 | 16 | 3 |
| Magnesium chloride | 24 | 24 | 24 | 24 | 16 | 3 |
| Calcium chloride | 24 | 24 | 24 | 24 | 16 | 3 |
| Ammonium sulfate | 24 | 24 | 24 | 24 | 16 | 3 |
| Potassium chloride | 24 | 24 | 24 | 24 | 16 | 3 |

TABLE 10

Production of xylose (g/L)

|  | 5 g/L | 10 g/L | 25 g/L | 35 g/L | 50 g/L | 100 g/L |
|---|---|---|---|---|---|---|
| Sodium chloride | 5 | 5 | 5 | 5 | 2 | 2 |
| Sodium sulfate | 5 | 5 | 5 | 5 | 2 | 2 |
| Magnesium chloride | 5 | 5 | 5 | 5 | 2 | 2 |
| Calcium chloride | 5 | 5 | 5 | 5 | 2 | 2 |
| Ammonium sulfate | 5 | 5 | 5 | 5 | 2 | 2 |
| Potassium chloride | 5 | 5 | 5 | 5 | 2 | 2 |

Tables 11 to 13 show results obtained by performing hydrolysis after addition of each water-soluble inorganic salt and then recovering the enzyme from the obtained solution component. It was revealed that the cellobiose-degrading activity and the xylan-degrading activity in the recovered enzyme decreased at the water-soluble inorganic salt concentrations of not less than 50 g/L. On the other hand, it was revealed that the cellobiose-degrading activity increased not less than 2-fold, the xylan-degrading activity increased not less than 1.2-fold, and the crystalline cellulose-degrading activity increased not less than 2-fold, in the cases where the water-soluble inorganic salt concentration was 5 to 35 g/L. On the other hand, it was revealed that the activities decreased in the cases where each water-soluble inorganic salt was added to a concentration of not less than 50 g/L.

TABLE 11

Cellobiose-degrading activity

|  | 5 g/L | 10 g/L | 25 g/L | 35 g/L | 50 g/L | 100 g/L |
|---|---|---|---|---|---|---|
| Sodium chloride | 2.4 | 2.5 | 2.6 | 2.7 | 2.1 | 1.0 |
| Magnesium sulfate | 2.5 | 2.5 | 2.5 | 2.5 | 2.1 | 1.0 |
| Magnesium chloride | 2.5 | 2.5 | 2.5 | 2.5 | 2.2 | 1.0 |
| Calcium chloride | 2.5 | 2.5 | 2.5 | 2.5 | 2.2 | 1.0 |

TABLE 11-continued

Cellobiose-degrading activity

|  | 5 g/L | 10 g/L | 25 g/L | 35 g/L | 50 g/L | 100 g/L |
|---|---|---|---|---|---|---|
| Ammonium sulfate | 2.5 | 2.5 | 2.5 | 2.5 | 2.2 | 1.0 |
| Potassium chloride | 2.4 | 2.4 | 2.4 | 2.4 | 2.1 | 1.0 |

TABLE 12

Xylan-degrading activity

|  | 5 g/L | 10 g/L | 25 g/L | 35 g/L | 50 g/L | 100 g/L |
|---|---|---|---|---|---|---|
| Sodium chloride | 2.5 | 3.0 | 3.1 | 3.1 | 2.4 | 1.0 |
| Magnesium sulfate | 2.4 | 2.9 | 3.1 | 3.1 | 2.1 | 1.0 |
| Magnesium chloride | 2.6 | 2.7 | 3.0 | 3.0 | 2.4 | 1.0 |
| Calcium chloride | 2.5 | 2.6 | 3.1 | 3.1 | 2.1 | 1.0 |
| Ammonium sulfate | 2.6 | 3.2 | 3.5 | 3.5 | 2.5 | 1.0 |
| Potassium chloride | 2.4 | 2.8 | 3.0 | 2.9 | 2.1 | 1.0 |

TABLE 13

Crystalline cellulose-degrading activity

|  | 5 g/L | 10 g/L | 25 g/L | 35 g/L | 50 g/L | 100 g/L |
|---|---|---|---|---|---|---|
| Sodium chloride | 0.25 | 0.4 | 0.8 | 0.8 | 0.15 | 0.1 |
| Magnesium sulfate | 0.22 | 0.45 | 0.6 | 0.6 | 0.15 | 0.1 |
| Magnesium chloride | 0.24 | 0.5 | 0.5 | 0.5 | 0.15 | 0.1 |
| Calcium chloride | 0.2 | 0.42 | 0.5 | 0.42 | 0.15 | 0.1 |
| Ammonium sulfate | 0.5 | 0.7 | 0.8 | 0.62 | 0.15 | 0.1 |
| Potassium chloride | 0.21 | 0.4 | 0.4 | 0.4 | 0.15 | 0.1 |

Example 3

Use of Sea Water as Water-soluble Inorganic Salt

In Examples 1 and 2, it could be confirmed that the activity of the enzyme recovered can be increased by addition of a 5 g/L to 35 g/L water-soluble inorganic salt. In view of this, whether "sea water" can be used as an alternative to the aqueous solution containing a water-soluble inorganic salt was studied. As the sea water, sea water collected near Misaki fishing port in Kanagawa pref. (pH 8.3; amount of solid dissolved, 3.2%) was used. The sea water was filtered using a Millex HV filter unit (33 mm; made of PVDF; pore size, 0.45 μm) before use. The pH of the sea water was adjusted to 5.0 using sulfuric acid (by addition of 50 mg of sulfuric acid per 1 L of the sea water). As a result of measurement of water-soluble inorganic salt concentrations in this sea water (pH 5) according to Reference Example 5, the sea water was found to contain 25 g/L sodium chloride, 3.2 g/L magnesium chloride and 2 g/L magnesium sulfate. That is, the sea water used in Example 3 was found to contain the water-soluble inorganic salts at a concentration of 30.2 g/L.

Subsequently, the above sea water (pH 5) was used as the water-soluble inorganic salt to perform hydrolysis of the pretreated products of biomass 1 and 2 prepared in Reference Example 1. To the pretreated products of biomass 1 and 2 (0.5 g), distilled water and the sea water (pH 5) were added, and 0.5 mL of the *Trichoderma*-derived cellulase prepared in Reference Example 3 was added, followed by further adding distilled water to a total weight of 10 g. The addition of sea water was carried out such that 2-fold dilution was attained in terms of the final concentration, that is, such that the water-soluble inorganic salt concentration was 15.1 g/L. pH adjustment was not necessary since the pH of the sea water had been preliminarily adjusted to 5. Hydrolysis and solid-liquid separation were carried out by the same procedures as in Comparative Example 1. Sugar concentrations (glucose and xylose concentrations) of the obtained solution component were measured according to the method described in Reference Example 2. The solution component was further filtered using a Millex HV filter unit (33 mm; made of PVDF; pore size, 0.45 μm), and the enzyme was recovered by the same procedure as in Comparative Example 1. Activities of the recovered enzyme were measured according to Reference Example 4. As a result, as shown in Table 14 and Table 15, it was revealed that addition of the sea water also improves the cellobiose-degrading activity, the crystalline cellulose-degrading activity and the xylan-degrading activity as compared to Comparative Example 1.

TABLE 14

Production of sugar/amount of enzyme recovered: pretreated product of cellulose 1

|  | Comparative Example 1 | Example 3 |
|---|---|---|
| Production of glucose (g/L) | 17 | 17 |
| Production of xylose (g/L) | 10 | 9 |
| Cellobiose-degrading activity | 2.3 | 3.0 |
| Crystalline cellulose-degrading activity | 0.22 | 0.65 |
| Xylan-degrading activity | 2.4 | 2.7 |

TABLE 15

Production of sugar/amount of enzyme recovered: pretreated product of cellulose 2

|  | Comparative Example 1 | Example 3 |
|---|---|---|
| Production of glucose (g/L) | 24 | 25 |
| Production of xylose (g/L) | 5 | 5 |
| Cellobiose-degrading activity | 1.2 | 2.5 |
| Crystalline cellulose-degrading activity | 0.1 | 0.7 |
| Xylan-degrading activity | 2.0 | 3.0 |

Example 4

Timing of Addition of Water-soluble Inorganic Salt in Hydrolysis Step

To determine the timing of addition of the water-soluble inorganic salt, the sugar production and the activities of the recovered enzyme were compared for the samples before addition of cellulase, immediately after addition of cellulase and 23 hours after addition of cellulase. Sodium chloride was used as the water-soluble inorganic salt, and it was added at a concentration of 10 g/L. As a result, as shown in Table 16, it was revealed that addition of the water-soluble inorganic salt before addition of, or immediately after addition (for example, at Hour 0 of the reaction) of, cellulase is preferred in view of increasing the activities, especially the crystalline cellulose-degrading activity, of the recovered enzyme.

TABLE 16

Timing of addition of an inorganic salt

|  | Before addition of cellulose (Hour 0) | After addition of cellulose (Hour 0) | After addition of cellulose (Hour 23) |
|---|---|---|---|
| Production of glucose (g/L) | 17 | 17 | 17 |
| Production of xylose (g/L) | 10 | 10 | 10 |
| Cellobiose-degrading activity | 2.7 | 2.7 | 2.3 |
| Xylan-degrading activity | 3.0 | 3.0 | 2.6 |
| Crystalline cellulose-degrading Activity | 0.5 | 0.5 | 0.25 |

Example 5

Concentration of Sugars and Removal of Monovalent Inorganic Salts Using Nanofiltration Membrane To study concentration of sugar and removal of monovalent inorganic salts using a nanofiltration membrane, mass preparation of a sugar liquid was carried out. In the mass preparation of a sugar liquid, 20 g of *Trichoderma*-derived cellulase was added to the pretreated product of cellulose 1 (1 kg), and sodium chloride was further added thereto to a final concentration of 10 g/L, followed by further adding distilled water to the resulting mixture to a total weight of 20 kg. Thereafter, the pH of the composition was adjusted with dilute sulfuric acid or dilute caustic soda to a value of 4.5 to 5.3. While the liquid was incubated such that a liquid temperature of 45 to 50° C. was maintained, and while dilute sulfuric acid and/or dilute caustic soda was/were added to the liquid such that the pH was maintained at 4.5 to 5.3, the enzyme was allowed to react with the pretreated product of biomass 2 for 24 hours. Using 10 L of the obtained enzymatic saccharification slurry liquid, press filtration was carried out by the following procedure. For the press filtration, a compact filter press apparatus (filter press MO-4, manufactured by Yabuta Industries Co., Ltd.) was used. As a filter cloth, a polyester woven fabric (T2731C, manufactured by Yabuta Industries Co., Ltd.) was used. After feeding 10 L of the slurry liquid to a small tank, a liquid inlet was opened to slowly feed the slurry liquid to a filtration chamber using an air pump (66053-3EB, manufactured by Taiyo International Corporation) under aeration with compressed air from the bottom. Subsequently, a compression step was carried out by swelling a diaphragm attached to the filtration chamber. The compression pressure was slowly increased to 0.5 MPa, and the apparatus was then left to stand for about 30 minutes to recover the filtrate. The total volume of the solution component obtained was 9.0 L. The remaining liquid component was lost because of the dead volume of the apparatus. As a result of measurement of sugar concentrations in the obtained solution component, the glucose concentration was 16 g/L and the xylose concentration was 10 g/L.

Subsequently, the solution component after solid-liquid separation was filtered through an ultrafiltration membrane, and thereby separated into the recovered enzyme and the sugar liquid component. The recovered enzyme was processed using a compact flat membrane filtration device (Sepa (registered trademark) CF II Med/High Foulant System, manufactured by GE) equipped with a flat ultrafiltration membrane having a molecular weight cutoff of 10000 (SEPA PW series, manufactured by GE, material of the functional surface: polyether sulfone). While the operating pressure was controlled such that the flow rate in the feed side was constantly 2.5 L/minute and the membrane flux was constantly 0.1 m/D, 5 L out of 9 L was filtered.

Using 1 L of the obtained sugar liquid, concentration through a nanofiltration membrane was carried out. As the nanofiltration membrane, DESAL-5L was used. This nanofiltration membrane was mounted on a compact flat membrane filtration device (Sepa (registered trademark) CF II Med/High Foulant System, manufactured by GE), and filtration treatment was carried out at a raw liquid temperature of 25° C. at a pressure of 3 MPa using a high-pressure pump. By this treatment, 0.2 L of a nanofiltration membrane concentrate and 0.8 L of a permeate (5-fold concentration) were obtained. The concentrations of glucose, xylose, sodium ions and chloride ions at this time were as shown in Table 17. It was revealed that concentrating sugars using a nanofiltration membrane enables reduction in the sodium chloride concentration with respect to the sugar concentration

TABLE 17

Concentration of sugars through a nanofiltration membrane

|  | Sugar liquid | Nanofiltration membrane concentrate 1 | Nanofiltration membrane permeate 1 |
|---|---|---|---|
| Glucose (g/L) | 16 | 76 | 1 |
| Xylose (g/L) | 10 | 30 | 5 |
| Sodium ion (g/L) | 3.9 | 6.0 | 3.3 |
| Chloride ion (g/L) | 6.1 | 9.2 | 5.3 |

Example 6

Concentration of Sugars and Removal of Monovalent Inorganic Salts Using Nanofiltration Membrane 2 (Diafiltration)

To 0.3 L of the concentrate obtained with a nanofiltration membrane in Example 6, 0.3 L of RO water was added to attain a total volume of 0.6 L, and the resulting solution was filtered through a nanofiltration membrane. By this, 0.3 L of a concentrate (nanofiltration membrane concentrate 2) and 0.3 L of a permeate (nanofiltration membrane permeate 2) were obtained (2-fold concentration). The concentrations of glucose, xylose, sodium ions and chloride ions were as shown in Table 18. It was revealed that filtration of the nanofiltration membrane concentrate further through a nanofiltration membrane enables further reduction in the concentrations of monovalent inorganic salts.

TABLE 18

Concentration of sugars through a nanofiltration membrane

|  | Nanofiltration membrane concentrate 1 (2-fold dilution) | Nanofiltration membrane concentrate 2 | Nanofiltration membrane permeate 2 |
|---|---|---|---|
| Glucose (g/L) | 38 | 74 | 2 |
| Xylose (g/L) | 15 | 25 | 5 |
| Sodium ion (g/L) | 3.0 | 3.9 | 2.1 |
| Chloride ion (g/L) | 4.6 | 5.5 | 3.7 |

Example 7

Recovery of Inorganic Salt Concentrate Using Reverse Osmosis Membrane

By passing 0.8 L of the permeate obtained with a nanofiltration membrane in Example 5 through an RO membrane, an inorganic salt concentrate was recovered. As the RO membrane, a cross-linked wholly aromatic reverse osmosis membrane "UTC80" (manufactured by Toray Industries, Inc.) was used. This RO membrane was mounted on a compact flat membrane filtration device (Sepa (registered trademark) CF II Med/High Foulant System, manufactured by GE), and filtration treatment was carried out at a raw liquid temperature of 25° C. at a pressure of 3 MPa using a high-pressure pump. By this treatment, 0.64 L of a permeate was obtained (5-fold concentration). The concentrations of glucose, xylose, sodium ions and chloride ions at this time were as shown in Table 19. It was revealed that, by filtering the permeate containing inorganic salts obtained with a nanofiltration membrane further through a reverse osmosis membrane, an inorganic salt concentrate can be obtained. Further, as a permeate, pure water containing neither inorganic salts nor sugars could be obtained.

TABLE 19

Recovery and reuse of water-soluble inorganic salts using an RO membrane

|  | Before nanofiltration treatment | Concentrate | Permeate |
| --- | --- | --- | --- |
| Glucose (g/L) | 1 | 5 | 0 |
| Xylose (g/L) | 5 | 25 | 0 |
| Sodium ion (g/L) | 3.3 | 16.5 | 0.1 |
| Chloride ion (g/L) | 5.3 | 26.5 | 0.1 |

Example 8

Preparation of Pretreated Product of Cellulose by Dilute Sulfuric Acid Treatment, Neutralization with Ammonia, and Hydrolysis Using Filamentous-fungal Cellulase Sugar cane bagasse as a cellulose-containing biomass was immersed in dilute aqueous sulfuric acid (1 wt %, 10 g/L), and subjected to treatment using an autoclave (manufactured by Nitto Koatsu Co., Ltd.) with stirring at 190° C. for 10 minutes. The treatment was carried out at a pressure of 10 MPa. Thereafter, solid-liquid separation was carried out using a compact filter press apparatus (a filter press manufactured by Yabuta Industries Co., Ltd.), to obtain a solution component (hereinafter referred to as sulfuric acid-treated liquid) (0.5 L) and a solid component. The solid concentration in the solid was about 50%. The solid was suspended again in RO water and subjected again to treatment using the compact filter press, to remove the sulfuric acid component contained in the solid. The solid obtained after removal of sulfuric acid is hereinafter referred to as the pretreated product of cellulose 3.

Subsequently, 6 mL of aqueous ammonia (28% solution, manufactured by Wako Pure Chemical Industries, Ltd.) was slowly added to 0.5 L of the sulfuric acid-treated liquid to perform neutralization to a pH of about 7. It can be assumed that, in this process, neutralization reaction between sulfate ions and ammonium ions produced about 13 g of ammonium sulfate (($NH_4$)$_2$$SO_4$) as a water-soluble inorganic salt. As a result of analysis of the sugar component in the sulfuric acid-treated liquid after the neutralization, 23 g/L xylose and 1 g/L glucose were found to be contained. This liquid is hereinafter referred to as the neutralized C5 sugar liquid.

Subsequently, the pretreated product of cellulose 3 was mixed with the neutralized C5 sugar liquid. To 1 g of solids of the pretreated product of cellulose 3, 10 mL of the neutralized C5 sugar liquid was added, and the resulting mixture was mixed (solid concentration, 10 wt %). Thereafter, the pH of the mixture was adjusted to 5 using dilute sulfuric acid and an aqueous sodium hydroxide solution. Subsequently, cellulase was added to the mixture to perform hydrolysis reaction. As the cellulase, "Accellerase Duet" manufactured by Genencor was purchased and used. In terms of the amount of cellulase added, 0.2 mL of the cellulase was added. The reaction was carried out under the same conditions as in Comparative Example 1 by mixing the mixture at 50° C. for 24 hours. The concentrations of sugars (glucose and xylose) contained in the obtained hydrolysate are shown in Table 20.

Thereafter, enzyme was recovered from the hydrolysate under the same conditions as in Comparative Example 1. Activities (the cellobiose-degrading activity, the Avicel-degrading activity and the xylan-degrading activity) of the recovered enzyme were measured according to Reference Example 4. The activities of the recovered enzyme are shown in Table 20.

Comparative Example 3

Preparation of Pretreated Product of Cellulose by Dilute Sulfuric Acid Treatment, Neutralization with Calcium Hydroxide, and Hydrolysis Using Filamentous Fungus-derived Cellulase For comparison with the above Example 8, the present Comparative Example shows a case where the neutralization was carried out with calcium hydroxide. By carrying out the neutralization with calcium hydroxide, calcium sulfate ($CaSO_4$), which is a salt of a sulfate ion and a calcium ion, is produced. Since calcium sulfate (lime) has a water solubility of about 2 g/L (25° C.), the hydrolysis in the present Comparative Example is not hydrolysis by addition of a water-soluble inorganic salt.

The Comparative Example 3 was carried out in the same manner as Example 8 except that calcium sulfate powder, instead of aqueous ammonia, was added for neutralization of the sulfuric acid-treated liquid to a pH of about 7, and that ammonium sulfate produced after neutralization was removed by centrifugation.

Subsequently, 3.7 g of calcium hydroxide (manufactured by Wako Pure Chemical Industries, Ltd.) was slowly added to 0.5 L of the sulfuric acid-treated liquid to perform neutralization to a pH of about 7. It can be assumed that, in this process, neutralization reaction between sulfate ions and calcium ions produced about 7 g of calcium sulfate, which is a water-insoluble inorganic salt. The sulfuric acid-treated liquid after neutralization was further centrifuged (3000 G, 20 minutes) to remove calcium sulfate as a water-insoluble inorganic salt, thereby obtaining the supernatant of the liquid. As a result of analysis of the sugar component of the supernatant, 22 g/L xylose and 1 g/L glucose were found to be contained. The supernatant is hereinafter referred to as the neutralized C5 sugar liquid (Comparative Example 2).

Subsequently, the pretreated product of cellulose 3 was mixed with the neutralized C5 sugar liquid (Comparative Example 2), and cellulase was added to the resulting mixture to perform hydrolysis by the same procedure as in Example 8. The concentrations of sugars (glucose and xylose) contained in the obtained hydrolysate are shown in Table 20.

Thereafter, enzyme was recovered from the hydrolysate under the same conditions as in Comparative Example 1. Activities (the cellobiose-degrading activity, the Avicel-degrading activity and the xylan-degrading activity) of the recovered enzyme were measured according to Reference Example 4. The activities of the recovered enzyme are shown in Table 20. As a result, it was revealed that the concentrations of sugars produced by hydrolysis with the filamentous fungus-derived cellulase were not largely different from those in Example 8. On the other hand, it was revealed that the activities of the recovered enzyme were higher in the case where neutralization was carried out using ammonia in Example 8, that is, in the case where hydrolysis was carried out in the presence of ammonium sulfate.

TABLE 20

Effect of dilute sulfuric acid treatment/neutralization with ammonia

|  | Example 7 | Comparative Example 3 |
|---|---|---|
| Production of glucose (g/L) | 65 | 63 |
| Production of xylose (g/L) | 28 | 27 |
| Cellobiose-degrading activity | 4.6 | 3.3 |
| Crystalline cellulose-degrading activity | 1.03 | 0.89 |
| Xylan-degrading activity | 4.8 | 2.4 |

Reference Example 6

Preparation of *Humicola* Cellulase

*Humicola* Cellulase was prepared by preculture and main culture of *Humicola grisea* (NBRC31242) in the same manner as in Reference Example 3. To the culture liquid prepared under the above-described conditions, β-glucosidase (Novozyme 188) was added at a protein weight ratio of 1/100, and the resulting mixture was used as the *Humicola* cellulase in the following Example and Comparative Example.

Comparative Example 4

Hydrolysis of Pretreated Product of Cellulose 3

Using the pretreated product of cellulose 3 of Example 8, hydrolysis and recovery of enzyme were carried out according to the description in Comparative Example 1, wherein no water-soluble inorganic salt was added. In this process, the *Trichoderma*-derived cellulase prepared in Reference Example 3 or the *Humicola*-derived cellulase prepared in Reference Example 6 was used as the filamentous fungus-derived cellulase for hydrolysis. The amounts of sugars produced and activities of the recovered enzyme are shown in Table 21.

TABLE 21

Hydrolysis of pretreated (dilute sulfuric acid-treated) product of cellulose

|  | *Trichoderma*-derived cellulose (Comparative Example 4) | *Humicola*-derived cellulose (Comparative Example 4) |
|---|---|---|
| Production of glucose (g/L) | 28 | 17 |
| Production of xylose (g/L) | 6 | 4 |
| Cellobiose-degrading activity | 0.8 | 0.6 |

TABLE 21-continued

Hydrolysis of pretreated (dilute sulfuric acid-treated) product of cellulose

|  | *Trichoderma*-derived cellulose (Comparative Example 4) | *Humicola*-derived cellulose (Comparative Example 4) |
|---|---|---|
| Crystalline cellulose-degrading activity | 0.1 | 0.05 |
| Xylan-degrading activity | 0.9 | 0.4 |

Example 9

Hydrolysis of Pretreated Product of Cellulose Supplemented with Water-soluble Inorganic Salt 3

Distilled water was added to the pretreated product of cellulose 3 (0.5 g) prepared in Example 8, and hydrolysis was carried out by the same procedure as in Example 1. The concentrations of sugars obtained and each activity of the recovered enzyme were measured. The relationship between the amount of each water-soluble inorganic salt added and the sugar production is shown in Table 23 and Table 24. It was found that the amounts of glucose and xylose produced were the same as in Comparative Example 4 (Table 21) in the cases of addition of the water-soluble inorganic salt to a concentration of 35 g/L or less, but that their production decreased in the cases where the concentration was 50 g/L or higher. This is considered to be due to high concentration of the water-soluble inorganic salt, which caused inhibition of the enzyme reaction. On the other hand, no large decrease in the produced sugar was observed within the range of 5 to 35 g/L.

TABLE 22

Production of glucose (g/L)

|  | 5 g/L | 10 g/L | 25 g/L | 35 g/L | 50 g/L | 100 g/L |
|---|---|---|---|---|---|---|
| Sodium chloride | 28 | 28 | 27 | 28 | 18 | 8 |
| Sodium sulfate | 27 | 27 | 28 | 26 | 17 | 6 |
| Magnesium chloride | 28 | 25 | 27 | 27 | 18 | 6 |
| Calcium chloride | 25 | 24 | 26 | 26 | 19 | 7 |
| Ammonium sulfate | 29 | 29 | 28 | 28 | 16 | 6 |
| Potassium chloride | 26 | 27 | 27 | 25 | 18 | 5 |

TABLE 23

Production of xylose (g/L)

|  | 5 g/L | 10 g/L | 25 g/L | 35 g/L | 50 g/L | 100 g/L |
|---|---|---|---|---|---|---|
| Sodium chloride | 6 | 6 | 6 | 6 | 4 | 2 |
| Sodium sulfate | 5 | 5 | 6 | 5 | 3 | 2 |
| Magnesium chloride | 6 | 6 | 6 | 6 | 4 | 2 |
| Calcium chloride | 6 | 6 | 6 | 6 | 4 | 2 |
| Ammonium sulfate | 6 | 6 | 6 | 6 | 4 | 2 |
| Potassium chloride | 6 | 6 | 6 | 6 | 4 | 2 |

Tables 24 to 26 show results obtained by performing hydrolysis after addition of each water-soluble inorganic salt and then recovering the enzyme from the obtained solution component. It was revealed that the cellobiose-degrading activity and the xylan-degrading activity of the recovered enzyme decreased at the water-soluble inorganic salt concentrations of not less than 50 g/L. On the other hand, it was revealed that the cellobiose-degrading activity increased not less than 2-fold, the xylan-degrading activity increased not less than 1.2-fold and the crystalline cellulose-degrading activity increased not less than 2-fold in the cases where the water-soluble inorganic salt concentration was 5 to 35 g/L. However, it was revealed that the activities decreased when the amount of water-soluble inorganic salt added was not less than 50 g/L.

TABLE 24

Cellobiose-degrading activity

| | 5 g/L | 10 g/L | 25 g/L | 35 g/L | 50 g/L | 100 g/L |
|---|---|---|---|---|---|---|
| Sodium chloride | 1.4 | 1.7 | 1.9 | 2.3 | 1.1 | 0.2 |
| Magnesium sulfate | 1.5 | 1.8 | 2.2 | 2.6 | 0.8 | 0.4 |
| Magnesium chloride | 1.4 | 1.6 | 2.0 | 2.5 | 0.9 | 0.5 |
| Calcium chloride | 1.6 | 1.7 | 2.3 | 2.5 | 0.7 | 0.4 |
| Ammonium sulfate | 1.9 | 2.1 | 2.4 | 2.4 | 0.5 | 0.6 |
| Potassium chloride | 1.8 | 2.0 | 2.4 | 2.6 | 0.2 | 0.6 |

TABLE 25

Xylan-degrading activity

| | 5 g/L | 10 g/L | 25 g/L | 35 g/L | 50 g/L | 100 g/L |
|---|---|---|---|---|---|---|
| Sodium chloride | 1.8 | 2.0 | 2.4 | 2.6 | 1.0 | 0.4 |
| Magnesium sulfate | 1.7 | 2.2 | 2.5 | 2.5 | 0.8 | 0.3 |
| Magnesium chloride | 2.0 | 2.0 | 2.3 | 2.4 | 0.7 | 0.4 |
| Calcium chloride | 1.5 | 2.1 | 2.4 | 2.6 | 0.6 | 0.3 |
| Ammonium sulfate | 2.0 | 2.2 | 2.2 | 2.7 | 0.7 | 0.4 |
| Potassium chloride | 1.9 | 2.3 | 2.6 | 2.5 | 0.8 | 0.3 |

TABLE 26

Crystalline cellulose-degrading activity

| | 5 g/L | 10 g/L | 25 g/L | 35 g/L | 50 g/L | 100 g/L |
|---|---|---|---|---|---|---|
| Sodium chloride | 0.2 | 0.5 | 0.5 | 0.7 | 0 | 0 |
| Magnesium sulfate | 0.2 | 0.6 | 0.8 | 0.8 | 0 | 0 |
| Magnesium chloride | 0.2 | 0.6 | 0.7 | 0.8 | 0 | 0 |
| Calcium chloride | 0.2 | 0.6 | 0.8 | 0.65 | 0 | 0 |
| Ammonium sulfate | 0.4 | 0.8 | 0.9 | 0.7 | 0 | 0 |
| Potassium chloride | 0.2 | 0.6 | 0.5 | 0.5 | 0 | 0 |

Example 10

Hydrolysis of Pretreated Product of Cellulose Supplemented with Water-soluble Inorganic Salt 4

Distilled water was added to the pretreated product of cellulose 3 (0.5 g) prepared in Example 8, and hydrolysis was carried out by the same procedure as in Example 1 except that the *Humicola*-derived cellulase described in Reference Example 6 was used. The concentrations of sugars obtained and each activity of the recovered enzyme were measured. The relationship between the amount of each water-soluble inorganic salt added and the sugar production is shown in Table 28 and Table 29. It was found that the amounts of glucose and xylose produced were the same as in Comparative Example 4 (Table 21) in the cases of addition of the water-soluble inorganic salt to a concentration of 35 g/L or less, but that their production decreased in the cases where the concentration was 50 g/L or higher. This is considered to be due to high concentration of the water-soluble inorganic salt, which caused inhibition of the enzyme reaction. On the other hand, no large decrease in the produced sugar was observed at 5 to 35 g/L.

TABLE 27

Production of glucose (g/L)

| | 5 g/L | 10 g/L | 25 g/L | 35 g/L | 50 g/L | 100 g/L |
|---|---|---|---|---|---|---|
| Sodium chloride | 17 | 17 | 17 | 16 | 12 | 5 |
| Magnesium sulfate | 17 | 17 | 17 | 16 | 12 | 4 |
| Magnesium chloride | 17 | 17 | 17 | 16 | 12 | 4 |
| Calcium chloride | 17 | 17 | 17 | 16 | 12 | 5 |
| Ammonium sulfate | 17 | 17 | 17 | 16 | 12 | 5 |
| Potassium chloride | 17 | 17 | 17 | 16 | 12 | 4 |

TABLE 28

Production of xylose (g/L)

| | 5 g/L | 10 g/L | 25 g/L | 35 g/L | 50 g/L | 100 g/L |
|---|---|---|---|---|---|---|
| Sodium chloride | 4 | 4 | 4 | 4 | 2 | 1 |
| Sodium sulfate | 4 | 4 | 4 | 4 | 2 | 2 |
| Magnesium chloride | 4 | 4 | 4 | 4 | 2 | 1 |
| Calcium chloride | 4 | 4 | 4 | 4 | 2 | 1 |
| Ammonium sulfate | 4 | 4 | 4 | 4 | 2 | 2 |
| Potassium chloride | 4 | 4 | 4 | 4 | 2 | 2 |

Tables 29 to 31 show results obtained by performing hydrolysis after addition of each water-soluble inorganic salt and then recovering the enzyme from the obtained solution component. It was revealed that the cellobiose-degrading activity and the xylan-degrading activity of the recovered enzyme decreased at the water-soluble inorganic salt concentrations of not less than 50 g/L. On the other hand, it was revealed that the cellobiose-degrading activity increased not less than 2-fold, the xylan-degrading activity increased not less than 1.2-fold and the crystalline cellulose-degrading activity increased not less than 2-fold in the cases where the water-soluble inorganic salt concentration was 5 to 35 g/L. However, it was revealed that the activities decreased when the amount of water-soluble inorganic salt added was not less than 50 g/L.

TABLE 29

Cellobiose-degrading activity

| | 5 g/L | 10 g/L | 25 g/L | 35 g/L | 50 g/L | 100 g/L |
|---|---|---|---|---|---|---|
| Sodium chloride | 1.2 | 1.7 | 2.2 | 2.5 | 0.9 | 0.6 |
| Magnesium sulfate | 1.2 | 1.6 | 2.1 | 2.4 | 0.6 | 0.6 |

TABLE 29-continued

Cellobiose-degrading activity

| | 5 g/L | 10 g/L | 25 g/L | 35 g/L | 50 g/L | 100 g/L |
|---|---|---|---|---|---|---|
| Magnesium chloride | 1.2 | 1.5 | 2.0 | 2.0 | 0.6 | 0.5 |
| Calcium chloride | 1.0 | 1.7 | 1.9. | 1.9. | 0.5 | 0.6 |
| Ammonium sulfate | 1.1 | 1.9 | 2.2 | 2.6 | 0.7 | 0.4 |
| Potassium chloride | 1.5 | 1.5 | 2.0 | 2.0 | 0.6 | 0.6 |

TABLE 30

Xylan-degrading activity

| | 5 g/L | 10 g/L | 25 g/L | 35 g/L | 50 g/L | 100 g/L |
|---|---|---|---|---|---|---|
| Sodium chloride | 1.5 | 1.8 | 2.1 | 2.4 | 1.2 | 0.6 |
| Magnesium sulfate | 1.2 | 1.7 | 2.6 | 2.2 | 1.1 | 0.5 |
| Magnesium chloride | 1.6 | 1.8 | 2.4 | 2.1 | 1.0 | 0.3 |
| Calcium chloride | 1.1 | 1.7 | 2.6 | 2.3 | 1.1 | 0.4 |
| Ammonium sulfate | 1.8 | 1.9 | 2.9 | 3.0 | 1.0 | 0.6 |
| Potassium chloride | 1.5 | 1.9 | 2.5 | 3.1 | 1.1 | 0.7 |

TABLE 31

Crystalline cellulose-degrading activity

| | 5 g/L | 10 g/L | 25 g/L | 35 g/L | 50 g/L | 100 g/L |
|---|---|---|---|---|---|---|
| Sodium chloride | 0.2 | 0.3 | 0.5 | 0.5 | 0 | 0 |
| Magnesium sulfate | 0.2 | 0.4 | 0.5 | 0.5 | 0 | 0 |
| Magnesium chloride | 0.2 | 0.3 | 0.4 | 0.5 | 0 | 0 |
| Calcium chloride | 0.2 | 0.4 | 0.4 | 0.4 | 0 | 0 |
| Ammonium sulfate | 0.2 | 0.5 | 0.6 | 0.6 | 0 | 0 |
| Potassium chloride | 0.2 | 0.3 | 0.5 | 0.5 | 0 | 0 |

Example 11

Ethanol Fermentation Using Sugar Liquid as Fermentation Feedstock

Using the nanofiltration membrane concentrate 2 of Example 6 as a fermentation feedstock, a test for ethanol fermentation by an yeast (*Saccharomyces cerevisiae* OC-2: wine yeast) was carried out. The yeast was precultured in YPD medium (2% glucose, 1% yeast extract (Bacto Yeast Extract, manufactured by BD), 2% polypeptone (manufactured by Nihon Pharmaceutical Co., Ltd)) for 1 day at 25° C. Subsequently, the obtained culture liquid was added to a nanofiltration membrane concentrate sugar liquid (glucose concentration, 74 g/L) whose pH was adjusted to 6 with sodium hydroxide, such that the concentration of the culture liquid was 1% (20 mL). After the addition of the microorganism, the culture liquid was incubated at 25° C. for 2 days. The concentration of ethanol accumulated in the culture liquid obtained by this operation was quantified by gas chromatography (by detection and calculation with a hydrogen flame ionization detector using Shimadzu GC-2010 Capillary GC TC-1 (GL Science) 15 meter L.×0.53 mm I. D., df 1.5 μm). As a result, the culture liquid could be confirmed to contain 24 g/L ethanol. That is, it could be confirmed that, by using the sugar liquid obtained by our method as a fermentation feedstock, ethanol can be produced.

Example 12

Lactic Acid Fermentation Using Sugar Liquid as Fermentation Feedstock

Using the nanofiltration membrane concentrate 2 of Example 6 as a fermentation feedstock, a test for lactic acid fermentation by the *Lactococcus lactis* JCM7638 strain (lactic acid bacterium) was carried out. The lactic acid bacterium was precultured in YPD medium (2% glucose, 1% yeast extract (Bacto Yeast Extract /BD), 2% polypeptone (manufactured by Nihon Pharmaceutical Co., Ltd)) for 1 day at 37° C. Subsequently, the obtained culture liquid was added to a nanofiltration membrane concentrate sugar liquid (glucose concentration, 74 g/L) whose pH was adjusted to 7 with sodium hydroxide, such that the concentration of the culture liquid was 1% (20 mL), and static culture of the *Lactococcus lactis* JCM7638 strain was carried out for 24 hours at a temperature of 37° C. The L-lactic acid concentration in the culture liquid was analyzed under the following conditions:

Column: Shim-Pack SPR-H (manufactured by Shimadzu Corporation)
Mobile phase: 5 mM p-toluenesulfonic acid (flow rate, 0.8 mL/min.)
Reaction solution: 5 mM p-toluenesulfonic acid, 20 mM Bis-Tris, 0.1 mM
EDTA-2Na (flow rate, 0.8 mL/min.)
Detection method: Electric conductivity
Temperature: 45° C.

As a result of the analysis, accumulation of 65 g/L L-lactic acid was observed, and it could be confirmed that lactic acid can be produced by using a sugar liquid as a fermentation feedstock.

INDUSTRIAL APPLICABILITY

The method for producing a sugar liquid can be used to produce a sugar liquid that is to be used as a fermentation feedstock for production of a chemical product from a cellulose-containing biomass. Further, sugar liquids produced by our methods can be used as fermentation feedstocks for various chemical products.

The invention claimed is:
1. A method of producing a sugar liquid comprising:
   (1) providing a pre-treated product of cellulose;
   (2) adding a water-soluble inorganic salt(s) to the pre-treated product of cellulose to a final salt(s) concentration of 5 g/L to 35 g/L;
   (3) hydrolyzing the product of (2) with a filamentous fungus-derived cellulase while maintaining the final salt(s) concentration of 5 g/L to 35 g/L to produce hydrolysate; and
   (4) subjecting the hydrolysate of (3) to solid-liquid separation and filtering the obtained solution component through an ultrafiltration membrane to recover the filamentous fungus-derived cellulase as a non-permeate and to obtain a sugar liquid as a permeate,
   wherein the final salt(s) concentration of 5 g/L to 35 g/L of the hydrolysate improves recovery of the filamentous fungus-derived cellulase in (4).
2. The method according to claim 1, wherein said water-soluble inorganic salt(s) of (2) is/are one or more selected from the group consisting of sodium salts, potassium salts, magnesium salts, calcium salts and ammonium salts.

3. The method according to claim 1, wherein said water-soluble inorganic salt(s) of (2) is/are one or more selected from the group consisting of sodium chloride, potassium chloride, sodium sulfate, magnesium chloride, magnesium sulfate, calcium chloride and ammonium sulfate.

4. The method according to claim 1, wherein said pretreated product of cellulose of (1) is one or more products selected from the group consisting of products obtained by hydrothermal treatment, dilute sulfuric acid treatment or alkali treatment.

5. The method according to claim 1, wherein said filamentous fungus-derived cellulase is *Trichoderma*-derived cellulase.

6. The method according to claim 1, further comprising filtering said sugar liquid of (4) through a nanofiltration membrane and/or reverse osmosis membrane to remove fermentation inhibitors as a permeate and to obtain a sugar concentrate as a non-permeate.

7. The method according to claim 6, further comprising filtering through a reverse osmosis membrane a permeate obtained by filtering said sugar liquid of (4) through a nanofiltration membrane; and reusing the inorganic salt concentrate obtained as a non-permeate as said water-soluble inorganic salt(s) of (2).

8. The method according to claim 2, wherein said water-soluble inorganic salt(s) of (2) is/are one or more selected from the group consisting of sodium chloride, potassium chloride, sodium sulfate, magnesium chloride, magnesium sulfate, calcium chloride and ammonium sulfate.

9. The method according to claim 2, wherein said pretreated product of cellulose of (1) is one or more products selected from the group consisting of products obtained by hydrothermal treatment, dilute sulfuric acid treatment or alkali treatment.

10. The method according to claim 3, wherein said pretreated product of cellulose of (1) is one or more products selected from the group consisting of products obtained by hydrothermal treatment, dilute sulfuric acid treatment or alkali treatment.

11. The method according to claim 2, wherein said filamentous fungus-derived cellulase is *Trichoderma*-derived cellulase.

12. The method according to claim 3, wherein said filamentous fungus-derived cellulase is *Trichoderma*-derived cellulase.

13. The method according to claim 4, wherein said filamentous fungus-derived cellulase is *Trichoderma*-derived cellulase.

14. The method according to claim 2, further comprising filtering said sugar liquid of (4) through a nanofiltration membrane and/or reverse osmosis membrane to remove fermentation inhibitors as a permeate and to obtain a sugar concentrate as a non-permeate.

15. The method according to claim 3, further comprising filtering said sugar liquid of (4) through a nanofiltration membrane and/or reverse osmosis membrane to remove fermentation inhibitors as a permeate and to obtain a sugar concentrate as a non-permeate.

16. The method according to claim 4, further comprising filtering said sugar liquid of (4) through a nanofiltration membrane and/or reverse osmosis membrane to remove fermentation inhibitors as a permeate and to obtain a sugar concentrate as a non-permeate.

17. The method according to claim 5, further comprising filtering said sugar liquid of (4) through a nanofiltration membrane and/or reverse osmosis membrane to remove fermentation inhibitors as a permeate and to obtain a sugar concentrate as a non-permeate.

18. The method according to claim 2, further comprising filtering through a reverse osmosis membrane a permeate obtained by filtering said sugar liquid of (4) through a nanofiltration membrane; and reusing the inorganic salt concentrate obtained as a non-permeate as said water-soluble inorganic salt(s) of (2).

19. The method according to claim 3, further comprising filtering through a reverse osmosis membrane a permeate obtained by filtering said sugar liquid of (4) through a nanofiltration membrane; and reusing the inorganic salt concentrate obtained as a non-permeate as said water-soluble inorganic salt(s) of (2).

20. The method according to claim 4, further comprising filtering through a reverse osmosis membrane a permeate obtained by filtering said sugar liquid of (4) through a nanofiltration membrane; and reusing the inorganic salt concentrate obtained as a non-permeate as said water-soluble inorganic salt(s) of (2).

\* \* \* \* \*